(12) United States Patent
Boss et al.

(10) Patent No.: US 11,299,710 B2
(45) Date of Patent: Apr. 12, 2022

(54) BROWN ADIPOCYTE PROGENITORS IN HUMAN SKELETAL MUSCLE

(71) Applicant: ENERGESIS PHARMACEUTICALS, INC., Cambridge, MA (US)

(72) Inventors: Olivier D. Boss, Boston, MA (US);
Mihaela Crisan, Rotterdam (NL);
Jean-Paul Giacobino, Geneva (CH)

(73) Assignee: ENERGESIS PHARMACEUTICALS, INC., Cambridge, MA (US)

( * ) Notice: Subject to any disclaimer, the term of this patent is extended or adjusted under 35 U.S.C. 154(b) by 182 days.

(21) Appl. No.: 16/409,926

(22) Filed: May 13, 2019

(65) Prior Publication Data

US 2020/0347353 A1    Nov. 5, 2020

Related U.S. Application Data

(62) Division of application No. 14/432,028, filed as application No. PCT/US2012/064389 on Nov. 9, 2012, now Pat. No. 10,301,595.

(60) Provisional application No. 61/558,152, filed on Nov. 10, 2011.

(51) Int. Cl.
*C12N 5/077* (2010.01)
*G01N 33/569* (2006.01)
*A61K 35/35* (2015.01)

(52) U.S. Cl.
CPC ............ *C12N 5/0653* (2013.01); *A61K 35/35* (2013.01); *G01N 33/56966* (2013.01); *C12N 2501/01* (2013.01); *C12N 2501/13* (2013.01); *C12N 2501/155* (2013.01); *C12N 2501/40* (2013.01); *G01N 2333/70503* (2013.01); *G01N 2333/70589* (2013.01); *G01N 2333/70596* (2013.01)

(58) Field of Classification Search
CPC .............. C12N 5/0653; C12N 2501/13; C12N 2501/01; C12N 2501/155; C12N 2501/40; G01N 33/56966
See application file for complete search history.

(56) References Cited

U.S. PATENT DOCUMENTS

| | | | |
|---|---|---|---|
| 8,455,204 B2 | 6/2013 | Boss et al. | |
| 10,301,595 B2 | 5/2019 | Boss et al. | |
| 2007/0264239 A1 | 11/2007 | Huard et al. | |
| 2008/0219957 A1 | 9/2008 | Lim et al. | |
| 2011/0104133 A1 | 5/2011 | Tseng et al. | |

FOREIGN PATENT DOCUMENTS

| | | | |
|---|---|---|---|
| CN | 1533504 A | 9/2004 | |
| CN | 102105789 A | 6/2011 | |
| WO | 2008013863 A2 | 1/2008 | |
| WO | 2009137613 A2 | 11/2009 | |
| WO | 2009151541 A1 | 12/2009 | |
| WO | WO-2009151541 A1 * | 12/2009 | ............... A61P 3/00 |

OTHER PUBLICATIONS

Russell et al., Brown adipocyte progenitor population is modified in obsess and diabetic skeletal muscle. International Journal of Obesity, vol. 36, No. 1 (2011) pp. 155-158. (Year: 2011).*
Zilberfarb et al., "Human immortalized brown adipocytes express functional β3-adrenoceptor coupled to lipolysis," Journal of Cell Science, 1997; vol. 110, pp. 801-807.
Almind et al., "Ectopic brown adipose tissue in muscle provides a mechanism for differences in risk of metabolic syndrome in mice," Proceedings of the National Academy of Sciences USA, Feb. 13, 2007; vol. 104, No. 7, pp. 2366-2371.
Anonymous, "Workshop Materials: 2011 Workshop," Retrieved from the Internet: http://secure.emmes.com/pactweb/content/workshop-materials (2012).
Billon et al., "Developmental Origins of the Adipocyte Lineage: New Insights from Genetics and Genomics Studies," Stem Cell Reviews and Reports, Humana Press Inc, New York, Mar. 2, 2011; vol. 8, No. 1, pp. 55-66.
Boss et al., "Recruitment of Brown Adipose Tissue as a Therapy for Obesity-Associated Diseases," Frontiers in Endocrinology, 2012; vol. 3, article 14, pp. 1-6.
Cannon et al., "Brown adipose tissue: function and physiological significance," Physiological Reviews, Jan. 2004, vol. 84, issue 1, pp. 277-359.
Cannon et al., "The biochemistry of an inefficient tissue: brown adipose tissue," Essays in Biochemistry, 1985; vol. 20, pp. 110-164.
Casteilla et al., "Adipose Tissue-Derived Cells: From Physiological to Regenerative Medicine," Diabetes & Metabolism, 2006; vol. 32, No. 5, pp. 393-401.
Champigny et al., "Regulation of UCP gene expression in brown adipocytes differentiated in primary culture. Effects of a new β-adrenoreceptor agonist," Molecular and Cellular Endocrinology, Jul. 1992; vol. 86, issues 1-2, pp. 73-82.
Cinti, Saverio, "Functional Anatomy of the 'Adipose Organ'," Cachexia and Wasting: A Modern Approach, Editors Mantovani et al., Springer, Milano publisher, 2006; Chapter 1.1, pp. 3-22.
Cipriani et al., "The Bile Acid Receptor GPBAR-1 (TGR5) Modulates Integrity of Intestinal Barrier and Immune Response to Experimental Colitis," PLOS One, 2011; vol. 6, issue 10, pp. 1-11.

(Continued)

*Primary Examiner* — Kara D Johnson
(74) *Attorney, Agent, or Firm* — Saliwanchik, Lloyd & Eisenschenk

(57) ABSTRACT

This invention relates to brown adipose tissue (BAT) progenitor cells and methods for isolating BAT progenitor cells from skeletal muscle. BAT progenitor cell surface markers and medium and agents for inducing cell differentiation into brown adipocytes are also provided. In some embodiments, the BAT progenitor cell expresses a first cell surface marker associated with endothelial cells, the first cell surface marker being detectable in an antibody based assay using a first antibody. In addition, the BAT progenitor cell can be substantially free of a second cell surface marker associated with endothelial cells, the second cell surface marker being substantially undetectable in said antibody based assay using a second antibody. The BAT progenitor cell can also be substantially free of additional cell surface markers.

17 Claims, 17 Drawing Sheets

Specification includes a Sequence Listing.

(56) References Cited

OTHER PUBLICATIONS

International Search Report issued in International Patent Application No. PCT/US2009/003217, dated Sep. 15, 2009.
International Search Report issued in International Patent Application No. PCT/US2012/064389, dated Jan. 28, 2013.
Corre et al., "Human bone marrow adipocytes support complete myeloid and lymphoid differentiation from human CD34 cells," British Journal of Haematology, Nov. 2004; vol. 127, issue 3, pp. 344-347.
Crisan et al., "A Reservoir of Brown Adipocyte Progenitors in Human Skeletal Muscle," Stem Cells, 2008; vol. 26, issue 9, pp. 2425-2433.
Cypess et al., "Identification and importance of brown adipose tissue in adult humans," New England Journal of Medicine, Apr. 9, 2009; vol. 360, No. 15, pp. 1509-1517.
Del Mar Gonzalez-Barroso et al., "The human uncoupling protein-1 gene (UCP1): present status and perspectives in obesity research," Obesity Reviews, Oct. 2000; vol. 1, issue 2, pp. 61-72.
Donnenberg, Albert D., "Adipose Derived Stem Cells: Phenotype, Function, and Clinical Targets," Retrieved from the Internet: https://secure.emmes.com/pactweb/system/files/08workshop_13_donnenberg.pdf (2008).
Extended European Search Report issued in European Patent Application No. 12847316.2, dated Mar. 5, 2015.
Feldmann et al., "UCP1 Ablation Induces Obesity and Abolishes Diet-Induced Thermogenesis in Mice Exempt from Thermal Stress by Living at Thermoneutrality," Cell Metabolism, Feb. 4, 2009; vol. 9, issue 2, pp. 203-209.
Foelimi-Adams et al., "Induction of uncoupling protein in brown adipose tissue: Synergy between norepinephrine and bioglitazone, an insulin-sensitizing agent," Biochemical Pharmacology, Sep. 13, 1996; vol. 52, issue 5, pp. 693-701.
Garstka et al., "Import of mitochondrial transcription factor A (TFAM) into rat liver mitochondria stimulates transcription of mitochondrial DNA," Nucleic Acids Research, Sep. 1, 2003; vol. 31, No. 17, pp. 5039-5047.
Girod et al., "Genome-wide prediction of matrix attachment regions that increase gene expression in mammalian cells," Nature Methods, Aug. 5, 2007; vol. 4, issue 9, pp. 747-773.
Goglia et al., "Morphometric-stereologic analysis of brown adipocyte differentiation in adult mice," American Journal of Physiology—Cell Physiology, Apr. 1, 1992; vol. 262, issue 4, pages C1018-C1023.
Jimenez et al., "Expression of uncoupling protein-3 in subsarcolemmal and intermyofibrillar mitochondria of various mouse muscle types and its modulation by fasting," European Journal of Biochemistry, Jun. 2002; vol. 269, issue 12, pp. 2878-2884.
Kawamata et al., "A G Protein-Coupled Receptor Responsive to Bile Acids," The Journal of Biological Chemistry, 2003; vol. 278, issue 11, pp. 9435-9440.
Kazantzis et al., "PAZ6 cells constitute a representative model for human brown pre-adipocytes," Frontiers in Endocrinology, Feb. 2012; vol. 3, article 13, pp. 1-9.
Klingenspor, Martin, "Cold-induced recruitment of brown adipose tissue thermogenesis," Experimental Physiology, Jan. 1, 2003; vol. 88, issue 1, pp. 141-148.
Kopecky et al., "Expression of the mitochondrial uncoupling protein gene from the aP2 gene promoter prevents genetic obesity," Journal of Clinical Investigation, Dec. 1995; vol. 96, issue 6, pp. 2914-2923.
Lehr et al., "The control of UCP1 is dissociated from that of PGC-1α or of mitochondriogenesis as revealed by a study using β-less mouse brown adipocytes in culture," FEBS Letters, Jul. 21, 2006; vol. 580, issue 19, pp. 4661-4666.
Lowell et al., "Development of obesity in transgenic mice after genetic ablation of brown adipose tissue," Nature, Dec. 30, 1993; vol. 366, pp. 740-742.
Lowry et al., "Protein Measurement with the Folin Phenol Reagent" Journal of Biological Chemistry, Nov. 1, 1951; vol. 193, issue 1, pp. 265-275.
Mensink et al., "Improved skeletal muscle oxidative enzyme activity and restoration of PGC-1α and PPARβ/δ gene expression upon rosiglitazone treatment in obese patients with type 2 diabetes mellitus," International Journal of Obesity (Lond), Aug. 2007; vol. 31, issue 8, pp. 1302-1310.
Nedergaard et al., "PPARgamma in the Control of Brown Adipocyte Differentiation," Biochimica et Biophysica Acta (BBA)—Molecular Basis of Disease, 2005; vol. 1740, issue 2, pp. 293-304.
Office Action issued in U.S. Appl. No. 12/994,590, dated Mar. 26, 2012.
Office Action issued in U.S. Appl. No. 12/994,590, dated Oct. 15, 2012.
Picó et al., "2-methoxyestradiol, an endogenous metabolite of 17β-estradiol, inhibits adipocyte proliferation," Molecular and Cellular Biochemistry, 1998; vol. 189, pp. 1-7.
Rodriguez et al., "Adipocyte differentiation of multipotent cells established from human adipose tissue," Biochemical and Biophysical Research Communications, Mar. 5, 2004; vol. 315, issue 2, pp. 255-263.
Rodriguez et al., "Transplantation of a Multipotent Cell Population from Human Adipose Tissue Induces Dystrophin Expression in the Immunocompetent mdx Mouse," Journal of Experimental Medicine, 2005; vol. 201, No. 9, pp. 1397-1405.
Rothwell et al., "A role for brown adipose tissue in diet-induced thermogenesis," Nature, Sep. 6, 1979; vol. 281, pp. 31-35.
Russell et al., "Brown Adipocyte Progenitor Population is Modified in Obese and Diabetic Skeletal Muscle," International Journal of Obesity, 2011; vol. 36, issue 1, pp. 155-158.
Seale et al., "PRDM16 controls a brown fat/skeletal muscle switch," Nature, 2008; vol. 454, pp. 961-968.
Sengenès et al., "Preadipocytes in the Human Subcutaneous Adipose Tissue Display Distinct Features from the Adult Mesenchymal and Hematopoietic Stem Cells," Journal of Cellular Physiology, 2005; vol. 205, issue 1, pp. 114-122.
Supplementary European Search Report issued in European Patent Application No. 09762837, dated May 30, 2012.
Traktuev et al., "A population of multipotent CD34-positive adipose stromal cells share pericyte and mesenchymal surface markers, reside in a periendothelial location, and stabilize endothelial networks," Circulation Research, Jun. 4, 2008; vol. 102, No. 1, pp. 77-85.
Tsukiyama-Kohara et al., "Adipose tissue reduction in mice lacking the translational inhibitor 4E-BP1," Nature Medicine, Oct. 2001; vol. 7, issue 10, pp. 1128-1132.
Van Marken Lichtenbelt et al., "Cold-activated brown adipose tissue in healthy men," New England Journal of Medicine, Apr. 9, 2009; vol. 360, No. 15, pp. 1500-1508.
Virtanen et al., "Functional brown adipose tissue in healthy adults," New England Journal of Medicine, Apr. 9, 2009; vol. 360, No. 15, pp. 1518-1525.
Wu et al., "Transcriptional activation of adipogenesis," Current Opinion in Cell Biology, Dec. 1, 1999; vol. 11, issue 6, pp. 689-694.
Zhou et al., "Cidea-deficient mice have lean phenotype and are resistant to obesity," Nature Genetics, Sep. 2003; vol. 35, No. 1, pp. 49-56.

\* cited by examiner

Adult muscle

☐ UCP1
■ leptin

Adult WAT

FIG. 5
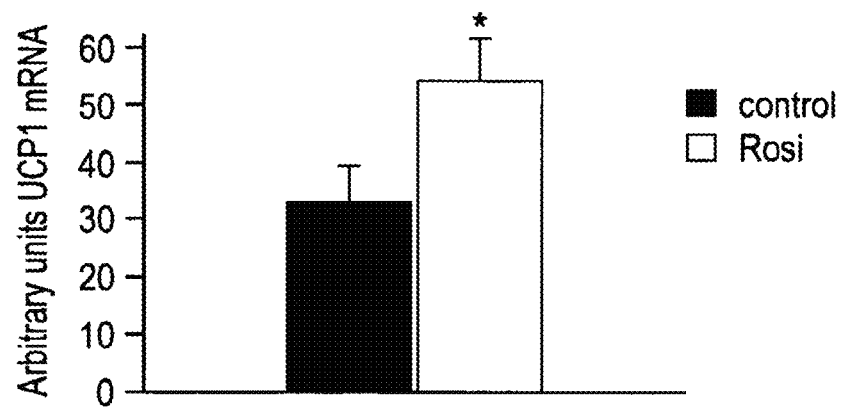
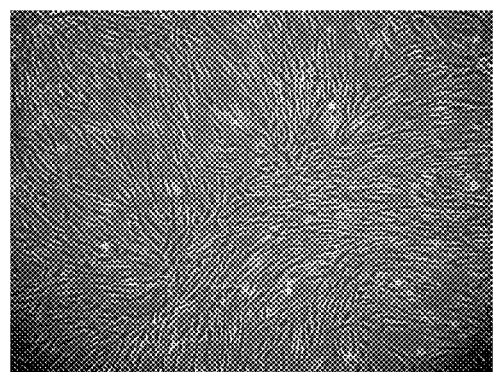
Fig. 6A. CD31- EMC309
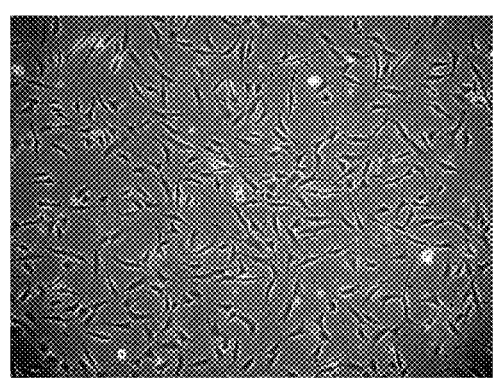
Fig. 6B. CD31- EMC314

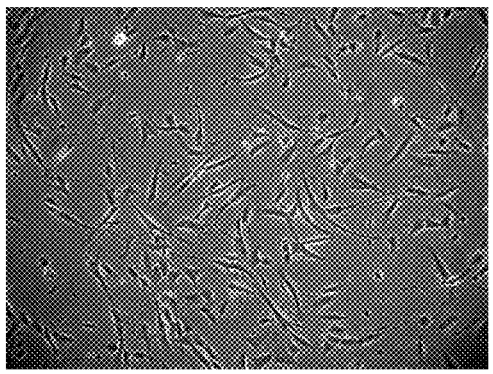
Fig. 7A. CD31+ EMC309
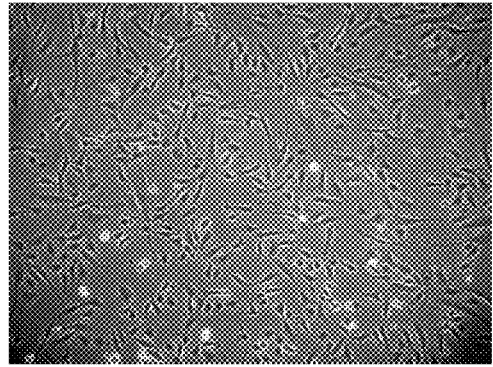
Fig. 7B. CD31+ EMC314
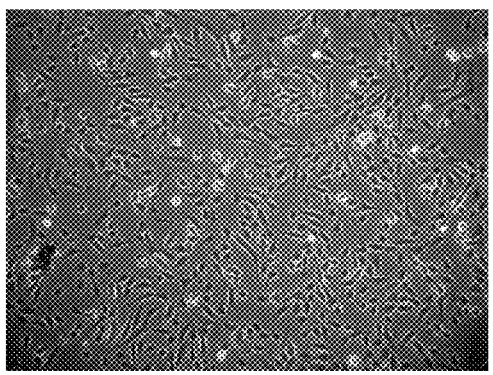
Fig. 8A. CD56+ EMC309
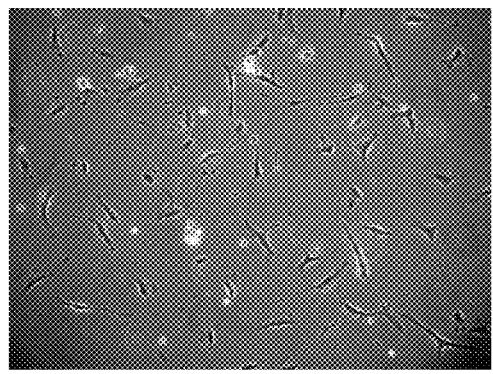
Fig. 8B. CD56+ EMC314

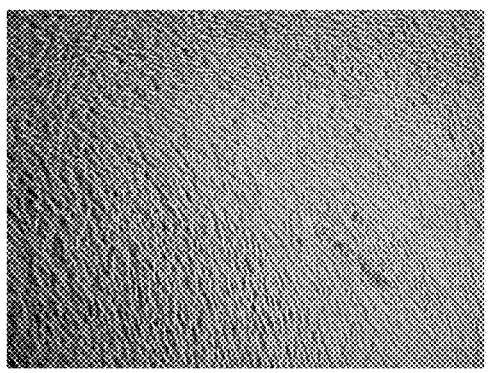
Fig. 9A. CD31⁻ cells (EMC309 P4) grown in EGM2, day 14
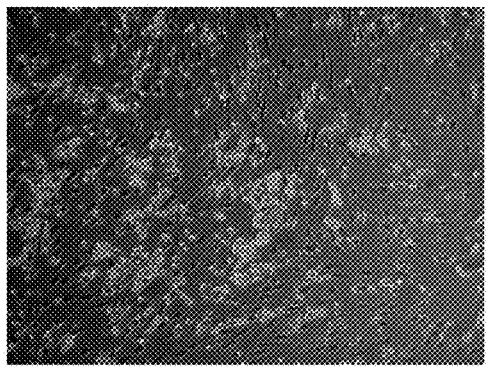
Fig. 9B. CD31⁻ cells (EMC309 P4) grown in MDM, day 14
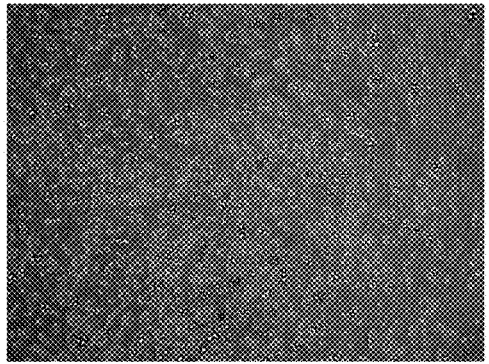
Fig. 9C. CD31⁻ cells (EMC309 P4) grown in MDM exposed to rosiglitazone (1 microM from day 0 to 14), day 14
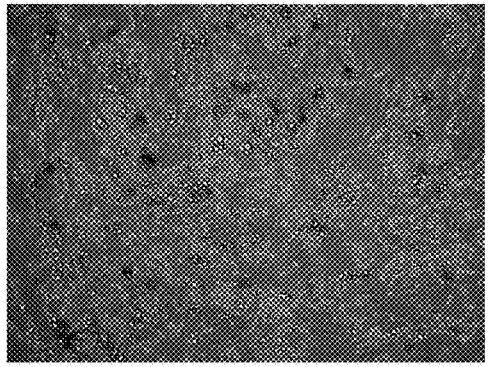
Fig. 9D. CD31⁻ cells (EMC309 P4) grown in MDM exposed to BMP7 (6 nM from day -2 to 0), day 14

Fig. 9E. CD31⁻ cells (EMC314 P3) grown in EGM2, day 14
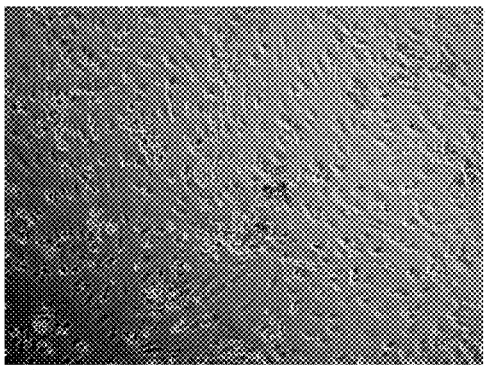
Fig. 9F. CD31⁻ cells (EMC314 P3) grown in MDM, day 14
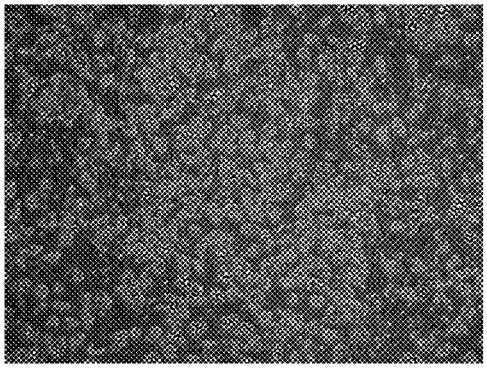
Fig. 9G. CD31⁻ cells (EMC314 P3) grown in MDM exposed to rosiglitazone (1 microM from day 0 to 14), day 14
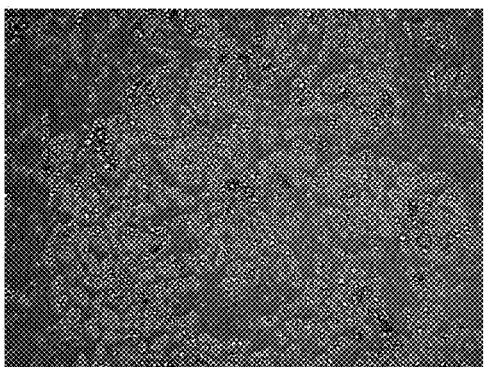
Fig. 9H. CD31⁻ cells (EMC314 P3) grown in MDM exposed to BMP7 (6 nM from day -2 to 0), day 14

Fig. 10A. CD31⁺ cells (EMC309 P6) grown in EGM2, day 14
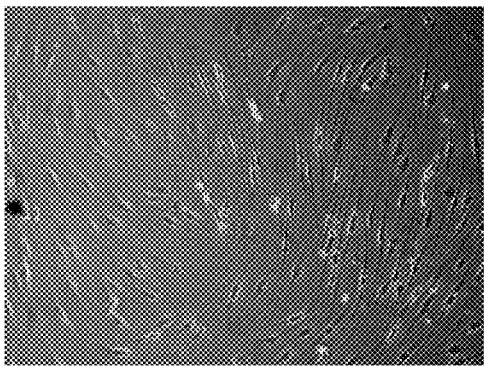
Fig. 10B. CD31⁺ cells (EMC309 P6) grown in MDM, day 14
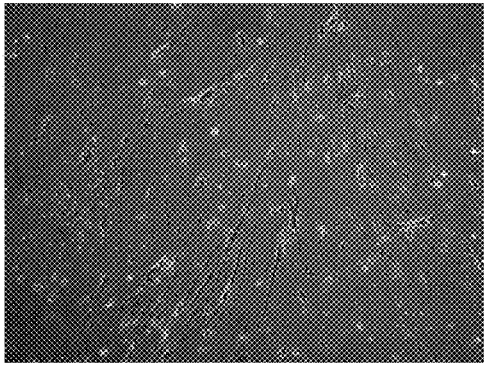
Fig. 10C. CD31⁺ cells (EMC309 P6) grown in MDM exposed to rosiglitazone (1 microM from day 0 to 14), day 14
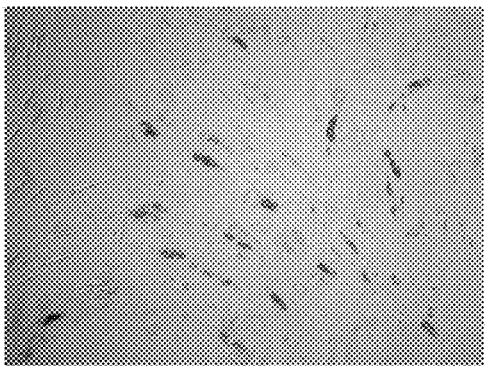
Fig. 10D. CD31⁺ cells (EMC309 P6) grown in MDM exposed to BMP7 (6 nM from day -2 to 0), day 14

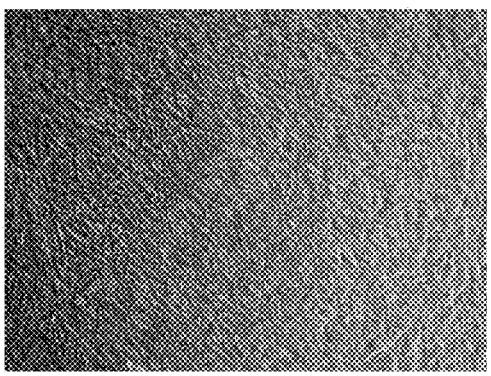
Fig. 10E. CD31+ cells (EMC314 P5) grown in EGM2, day 14
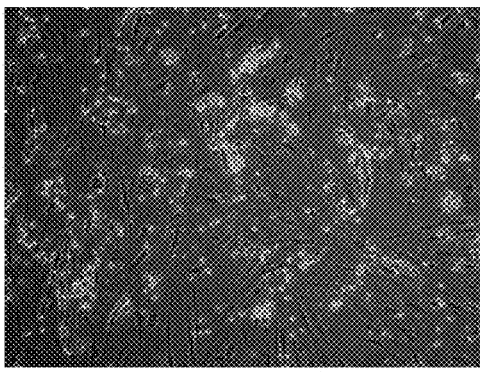
Fig. 10F. CD31+ cells (EMC314 P5) grown in MDM, day 14
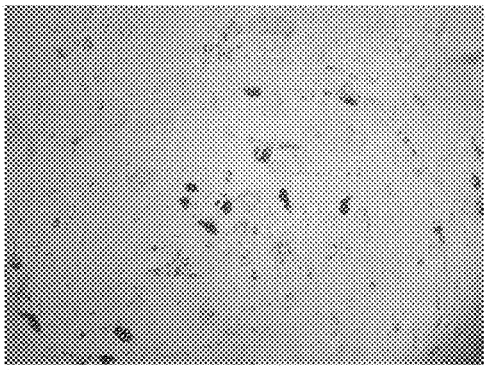
Fig. 10G. CD31+ cells (EMC314 P5) grown in MDM exposed to rosiglitazone (1 microM from day 0 to 14), day 14
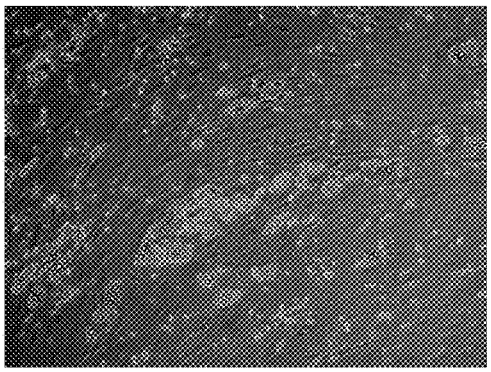
Fig. 10H. CD31+ cells (EMC314 P5) grown in MDM exposed to BMP7 (6 nM from day -2 to 0), day 14

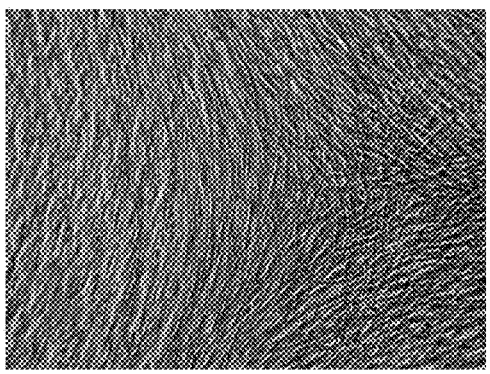
Fig. 11A. CD56+ cells (EMC309 P4) grown in EGM2, day 14
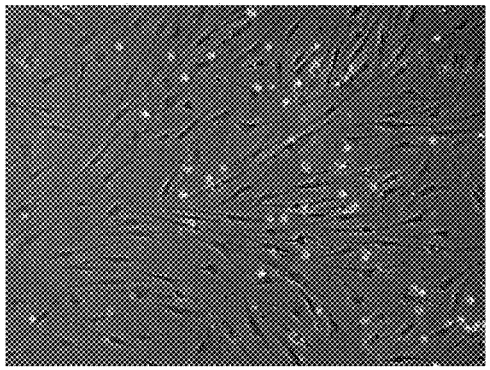
Fig. 11B. CD56+ cells (EMC309 P4) grown in MDM, day 14
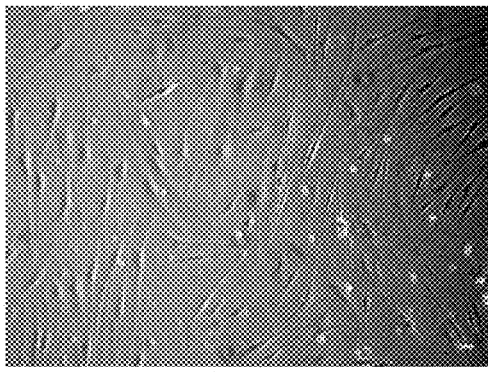
Fig. 11C. CD56+ cells (EMC309 P4) grown in MDM exposed to rosiglitazone (1 microM from day 0 to 14), day 14
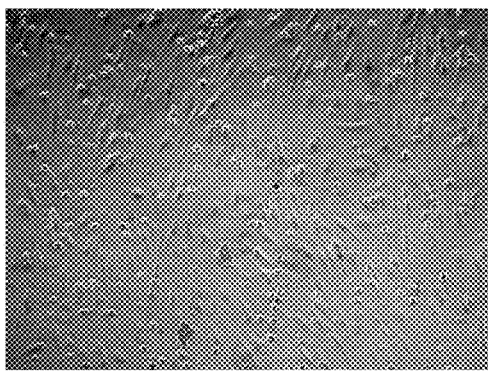
Fig. 11D. CD56+ cells (EMC309 P4) grown in MDM exposed to BMP7 (6 nM from day -2 to 0), day 14

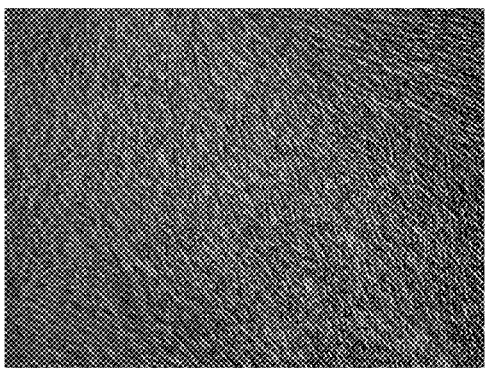
Fig. 11E. CD56+ cells (EMC314 P5) grown in EGM2, day 14
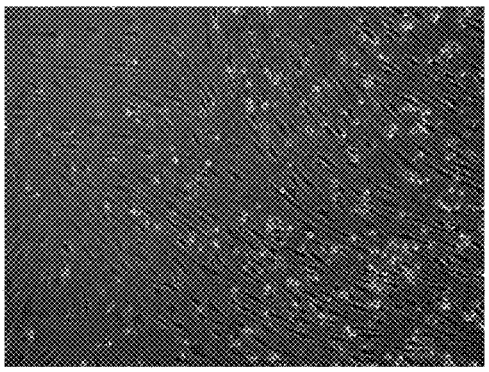
Fig. 11F. CD56+ cells (EMC314 P5) grown in MDM, day 14
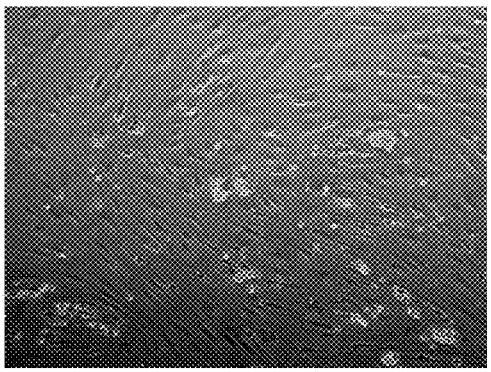
Fig. 11G. CD56+ cells (EMC314 P5) grown in MDM exposed to rosiglitazone (1 microM from day 0 to 14), day 14
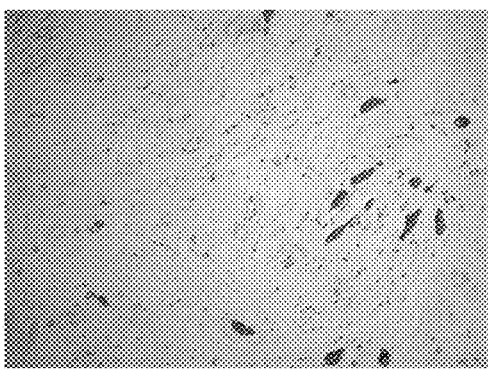
Fig. 11H. CD56+ cells (EMC314 P5) grown in MDM exposed to BMP7 (6 nM from day -2 to 0), day 14

FIG. 16
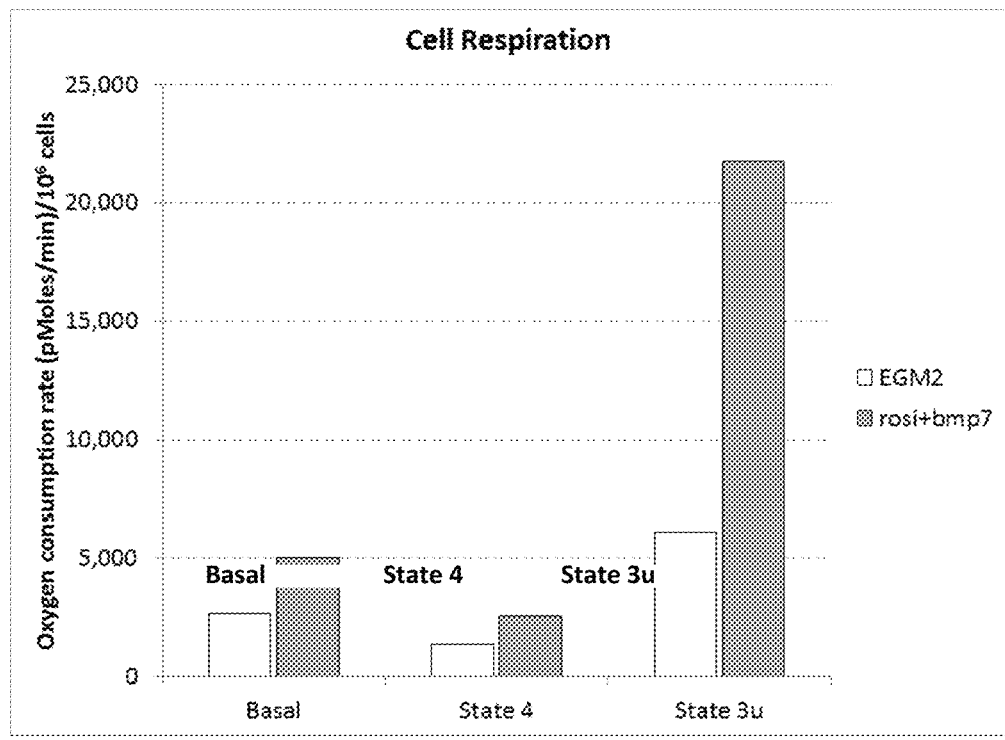
FIG. 17A  Minimal Differentiation Media (no rosiglitazone)
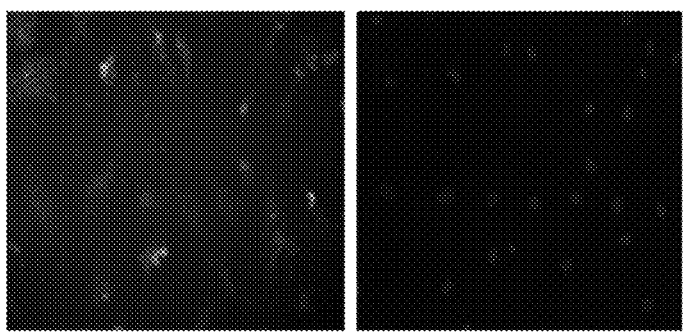
FIG. 17B  Reference Differentiation Media (with rosiglitazone)
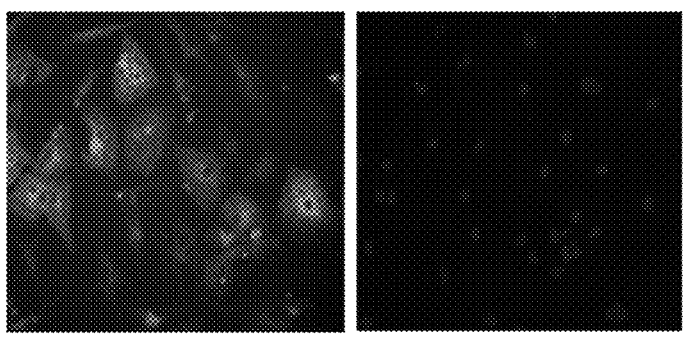

BROWN ADIPOCYTE PROGENITORS IN HUMAN SKELETAL MUSCLE

CROSS REFERENCE TO RELATED APPLICATIONS

This application is a divisional patent application of U.S. patent application Ser. No. 14/432,028, filed Mar. 27, 2015, now U.S. Pat. No. 10,301,595, which is a U.S. national phase application of PCT International Patent Application No. PCT/US2012/064389, filed on Nov. 9, 2012, which claims priority to and the benefit of U.S. Provisional Patent Application No. 61/558,152, filed on Nov. 10, 2011, each of which is incorporated herein by reference in their entireties.

TECHNICAL FIELD

This invention relates to brown adipose tissue (BAT) progenitor cells and methods for isolating BAT progenitor cells from skeletal muscle. The invention also relates to BAT progenitor cell surface markers and medium and agents for inducing cell differentiation. The invention is useful for the study, prevention and treatment of various metabolic diseases such as obesity, type 2 diabetes, insulin-resistance and dyslipidemia.

BACKGROUND

The epidemic of obesity is closely associated with increases in the prevalence of diabetes, hypertension, coronary heart diseases, cancer and other disorders. The role of white adipose tissue is to store lipids, and it is associated with obesity. The role of the brown adipose tissue ("BAT") is effectively the opposite. It is specialized in lipid combustion and the dissipation of energy as heat. Indeed, the brown adipocyte contains lots of mitochondria (in which cellular combustion occurs) and uniquely expresses BAT uncoupling protein-1 ("UCP1"). UCP1 acts as an uncoupler of oxidative phosphorylation, resulting in dissipation of energy as heat. The sympathetic nervous system stimulates mitochondriogenesis and UCP1 expression and activity. BAT-associated thermogenesis in rodents is increased upon exposure to low temperature (e.g., preventing hypothermia) or as a result of overeating, burning excess absorbed fat and preventing weight gain. BAT, by modifying susceptibility to weight gain and by consuming large amounts of glucose, also improves insulin sensitivity. It therefore plays an important role in the maintenance of body temperature, energy balance and glucose metabolism.

Experiments with transgenic animals support the potential anti-obesity properties of BAT. For example, the genetic ablation of BAT has been reported to cause obesity, while genetic increase in the amount and/or function of BAT (and/or UCP1 expression) reportedly promotes a lean and healthy phenotype. Specifically, mice with a higher amount of BAT gain less weight and are more insulin-sensitive than control mice. Recently, ectopic BAT depots were evidenced in the mouse muscle, which were proposed to provide a genetic-based mechanism of protection from weight gain and metabolic syndrome.

Although UCP1 is reported to play a role in the control of energy balance in rodents and UCP1-expressing BAT is present in human neonates, it has long been thought that there was no physiologically relevant UCP1 expression in adult humans Indeed, UCP1-expressing BAT was thought to disappear early in life, and adult humans were thought to be devoid of BAT.

As such, a need exists to carefully identify and study ways to provide more BAT in the adult body and/or stimulate UCP1 expression, for the study, prevention and treatment of various metabolic diseases such as obesity, type 2 diabetes, insulin-resistance dyslipidemia and type 1 diabetes.

SUMMARY

Applicants have for the first time identified the presence of cells in various tissues that are capable of differentiating into brown adipocytes. In one aspect, Applicants have identified a population of such cells, which Applicants refer to as BAT progenitor cells, in skeletal muscle. The present disclosure provides methods for sorting cells from various tissues to identify and isolate BAT progenitor cells. In some embodiments, BAT progenitor cells are isolated from human skeletal muscle. Methods are provided for differentiating BAT progenitor cells in vitro and in vivo into brown adipocytes. In some embodiments, BAT progenitor cells can be caused to differentiate in vivo into brown adipocytes in a human subject. The present invention also relates to BAT progenitor cell surface markers (e.g., CD31 and CD34) and medium and agents for inducing cell differentiation (e.g., PPARγ agonist and BMP7).

In some embodiments, BAT progenitor cells of the present disclosure can be expanded in culture. In another aspect, differentiated BAT progenitor cell UCP1 mRNA expression is increased by agents such as cell-permeating cAMP derivatives, peroxisome-proliferator-activated receptor (PPAR such as PPARγ) agonists, and the like. BAT progenitor cells that have been differentiated into brown adipocytes may, in some embodiments, contain large amounts of mitochondrial transcription factor A (mtTFA) and PPARγ coactivator-1α (PGC-1α), which are both involved in the control of mitochondriogenesis, as well as of mitochondrial marker cytochrome oxidase IV (COX IV). Differentiated BAT progenitor cells can exhibit one or more of the following characteristics: high levels of UCP1 expression, high levels of uncoupled respiration, high respiration rate, high metabolic rate. Applicants provide differentiated cells that are equipped to metabolize glucose, oxidize fatty acids, and dissipate energy as heat via uncoupling of oxidative phosphorylation.

The present disclosure provides methods for detection of UCP1 mRNA in the skeletal muscle of adult humans, and methods for increasing its expression in vivo. Although prior studies concerning UCP1 expression in adult humans have focused on white adipose tissue, applicants disclose the existence in, and isolation from, human skeletal muscle of brown adipose progenitor cells with a substantial potential for UCP1 expression. In some embodiments, this reservoir of BAT progenitor cells can be utilized for modulation of energy dissipation and for treating obesity, diabetes, and metabolic diseases.

In some aspects, this disclosure provides methods for the identification of BAT progenitor cells in human skeletal muscle and methods to isolate these cells from human skeletal muscle samples. Also provided are conditions and agents (e.g., compounds, proteins, biologicals, and the like) that promote the differentiation of these progenitor cells to brown adipocytes in vitro, in vivo, or both. Methods are provided for using these conditions and agents to treat metabolic diseases such as obesity, type 2 diabetes, insulin-resistance, dyslipidemia, and the like.

The present disclosure provides assays that allow identification of agents (e.g., compounds, proteins, biologicals, and the like) that induce the expression of the UCP1 gene, promote the differentiation of BAT progenitor cells into brown adipocytes in vitro, promote the differentiation of BAT progenitor cells to brown adipocytes in vivo, or combinations of these activities. According to some embodiments, agents identified in this manner can be used to treat metabolic diseases such as obesity, type 2 diabetes, insulin-resistance, dyslipidemia, and the like.

In one aspect, a brown adipose tissue (BAT) progenitor cell is provided. The BAT progenitor cell is isolated from human skeletal muscle and capable of differentiating into brown adipocyte. The BAT progenitor cell expresses a first cell surface marker associated with endothelial cells, said first cell surface marker being detectable in an antibody based assay using a first antibody. In addition, the BAT progenitor cell is substantially free of a second cell surface marker associated with endothelial cells, said second cell surface marker being substantially undetectable in said antibody based assay using a second antibody. In certain embodiments, the BAT progenitor cell can be substantially free of at least one of a third, fourth, and fifth cell surface marker. For example, the BAT progenitor cell can be substantially free of a third cell surface marker associated with hematopoietic cells, said third cell surface marker being substantially undetectable in said antibody based assay using a third antibody. The BAT progenitor cell can be substantially free of the third cell surface marker and/or a fourth cell surface marker associated with myogenic cells, said fourth cell surface marker being substantially undetectable in said antibody based assay using a fourth antibody. The BAT progenitor cell may be substantially free of the third and/or fourth cell surface marker, and/or a fifth cell surface marker associated with pericytes, said fifth cell surface marker being substantially undetectable in said antibody based assay using a fifth antibody.

In a further aspect, the present invention features a population of cells isolated from skeletal muscle, comprising at least one BAT progenitor cell as described herein.

In another aspect, a method for identifying a BAT progenitor cell is provided. The method includes: providing a population of cells isolated from skeletal muscle; contacting the population of cells with a first and a second antibody that are specific to a first and a second cell surface marker, respectively, wherein the first and second cell surface markers are each associated with endothelial cells; and determining, in an antibody based assay, a BAT progenitor cell that expresses the first cell surface marker and is substantially free of the second cell surface marker. In some embodiments, the method can further include at least one of: contacting the population of cells with a third antibody specific to a third cell surface marker associated with hematopoietic cells, said third cell surface marker being substantially undetectable in said antibody based assay using the third antibody; contacting the population of cells with a fourth antibody specific to a fourth cell surface marker associated with myogenic cells, said fourth cell surface marker being substantially undetectable in said antibody based assay using the fourth antibody; and/or contacting the population of cells with a fifth antibody specific to a fifth cell surface marker associated with pericytes, said fifth cell surface marker being substantially undetectable in said antibody based assay using the fifth antibody. In certain embodiments, the method can further include separating the population of cells by selecting cells that express the first cell surface marker and that do not express the second cell surface markers. In some embodiments, the method can include separating the population of cells by selecting cells that express the first cell surface marker and that do not express the second, and at least one of the third, fourth and fifth cell surface markers. For example, said selecting can include selecting cells that express CD34 and that do not express CD31, CD45, CD56 or CD146. The method can also include isolating the BAT progenitor cell and/or culturing the BAT progenitor cell in a proliferation medium, thereby expanding BAT progenitor cells ex vivo.

In yet another aspect, a method for inducing differentiation of BAT progenitor cells into brown adipocytes is provided. The method includes: providing the BAT progenitor cell described herein; exposing the BAT progenitor cell to a differentiation medium; and culturing the BAT progenitor cell in the differentiation medium to induce the BAT progenitor cell to differentiate into a brown adipocyte.

In still another aspect, the present invention features a method for treating a metabolic disease or condition in a patient. The method includes: obtaining BAT progenitor cells from skeletal muscle of the individual or a donor; propagating the BAT progenitor cells by culturing in a medium; and transplanting the cultured cells into the individual. In certain embodiments, the method can further include inducing differentiation of the BAT progenitor cells into brown adipocytes via ex vivo culturing in a differentiation medium. In various embodiments, the metabolic disease is obesity, overweight, impaired glucose tolerance, insulin-resistance, type 2 diabetes, dyslipidemia, hypertension, cardiovascular disease, metabolic syndrome, Prader-Willi Syndrome, or type 1 diabetes.

In a further aspect, a method for identifying an agent that induces differentiation of a BAT progenitor cell into a brown adipocyte is provided. The method includes: providing the BAT progenitor cell described herein; contacting the BAT progenitor cell with an agent; determining if the BAT progenitor cell exhibits an indicator of differentiation into a brown adipocyte. In some embodiments, the indicator of differentiation can be an increase in one or more of the following: expression of UCP1 protein or mRNA, expression of FABP4 (aP2) protein or mRNA, expression of PPARγ2 protein or mRNA, expression of mtTFA protein or mRNA, expression of PGC-1α protein or mRNA, uncoupled respiration, respiration rate, metabolic rate, glucose utilization rate, fatty acid oxidation rate, and a combination thereof.

In still a further aspect, a method for identifying an agent that induces expression or activity levels of UCP1 is provided. The method includes: providing the BAT progenitor cell described herein; contacting the BAT progenitor cell with an agent; determining if the BAT progenitor cell exhibits an increase in UCP1 expression or activity.

The present invention also includes use of an agent identified using any one of the methods described herein, in the manufacture of a medicament for the treatment of a metabolic disease, and/or for the treatment or prevention of hypothermia in a patient.

In some embodiments, the first cell surface marker can be CD34 and the first antibody can be an anti-CD34 antibody. In one embodiment, the second cell surface marker can be CD31 and the second antibody can be an anti-CD31 antibody. The third cell surface marker, for example, can be CD45 and the third antibody can be an anti-CD45 antibody. The fourth cell surface marker, for example, can be CD56 and the fourth antibody can be an anti-CD56 antibody. The fifth cell surface marker, for example, can be CD146 and the fifth antibody can be an anti-CD146 antibody.

In various embodiments, the BAT progenitor cell can differentiate into the brown adipocyte in a differentiation medium. For example, the differentiation medium can be Minimal Differentiation Medium (MDM). The differentiation medium can further comprise a peroxisome proliferator-activated receptor gamma (PPARγ) agonist and/or bone morphogenic protein-7 (BMP7). In some embodiments, the BMP7, prior to the addition of the differentiation medium, can be present in a proliferation medium which allows proliferation of the BAT progenitor cell.

Additional aspects of the present invention include isolated BAT progenitor cells, primary culture thereof, established or immortalized cell line therefrom, cultured BAT progenitor cells or cell lines, transfected or transducted or infected or transformed cells or cell lines, and any cells or cultures that may differentiate from such BAT progenitor cells or cell lines or transformants. These and other features of the present disclosure are set forth herein.

BRIEF DESCRIPTION OF THE DRAWINGS

FIGS. 2A, 2B, 2C, 2D: Phase contrast; scale bar: 50 μm. FIG. 2E shows quantitative RT-PCR determination of UCP1 (empty columns) and leptin (gray columns) mRNA expression in CD34+ cells in primary culture (PC) or expanded up to passage 3 (P3). FIG. 2F shows immunohistochemical determination of UCP1 levels.

FIG. 3A shows uncoupling of mitochondrial respiration in isolated fetal muscle CD34+ cells and in human adult white adipocytes grown in primary culture and freshly trypsinized. FIG. 3B: The effects of cAMP derivatives on UCP1 mRNA expression in CD34+ cells in PC or expanded up to P3. FIG. 3C: The effects of rosiglitazone (Rosi) 1 μM on UCP1 mRNA expression in CD34+ cell PC or P3.

FIGS. 4A, 4C: Phase contrast; scale bar: 50 μm.

FIG. 5 shows effects of rosiglitazone on UCP1 mRNA expression in human skeletal muscle.

FIGS. 6A-6B show CD31− cell population before expansion (FIG. 6A: EMC309, passage 2; FIG. 6B: EMC314, passage 1).

FIGS. 7A-7B show CD31+ cell population before expansion (FIG. 7A: EMC309, passage 4; FIG. 7B: EMC314, passage 3).

FIGS. 8A-8B show CD56+ cell population before expansion (FIG. 8A: EMC309, passage 1; FIG. 8B: EMC314, passage 3).

FIGS. 9A-9H show that CD31− cell population differentiate into brown adipocytes (FIGS. 9A-9D: EMC309, passage 4 at d14; FIGS. 9E-9H: EMC314, passage 3 at d14).

FIGS. 10A-10H show that CD31+ cells do not differentiate into adipocytes (FIGS. 10A-10D: EMC309, passage 6 at d14; FIGS. 10E-10H: EMC314, passage 5 at d14).

FIGS. 11A-11H show that CD56+ cells do not differentiate into adipocytes (FIGS. 11A-11D: EMC309, passage 6 at d14; FIGS. 11E-11H: EMC314, passage 5 at d14).

FIG. 12A: CD31−, CD31+, CD56+ cells. FIG. 12B: EMC309/314 cells.

FIG. 16 shows respiration of the CD31− cells. The CD31− cells differentiated into brown adipocytes (gray bars) have higher levels of mitochondrial uncoupling, or proton leak (State 4 respiration), as well as maximal (uncoupled) respiration (State 3u) vs. non-differentiated cells (EGM2, white bars).

FIGS. 17A-17B show the quantification of UCP1 in CD31− cells by fluorescence immunohistochemistry. Differentiation of CD31− cells into brown adipocytes without (FIG. 17A) or with (FIG. 17B) rosiglitazone.

DETAILED DESCRIPTION

Figure 1A:
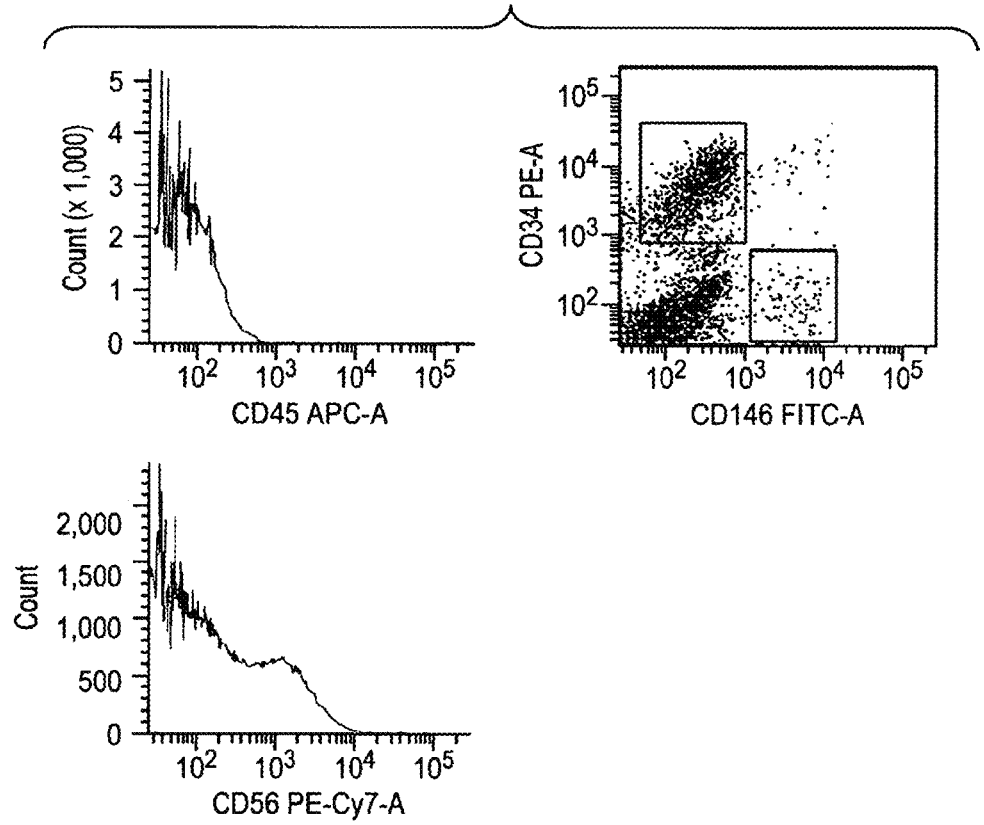
FIGS. 1A-1B show immunohistochemical description (FIG. 1B) and FACS analysis and sorting (FIG. 1A) of stroma-vascular cells in human fetal muscle.

The present disclosure provides methods for identifying and isolating BAT progenitor cells in and from various tissues, including, in some embodiments, the identification of common brown adipocyte progenitor cells in human skeletal muscle and isolation of such cells from human skeletal muscle samples. In some embodiments, the cell sorting can be done by immunohistochemical analysis of cell surface markers such as one or more of cluster of differentiation/designation ("CD") molecules CD31, CD34, CD45, CD56, and CD146. CD31 and CD34 can be used to identify endothelial cells. Hematopoietic cells and myogenic progenitors can be sorted based on identification of CD45 and CD56, respectively, on their cell surfaces. CD146 can be used to identify pericytes. In one aspect, expression of CD34 identifies a cell as a progenitor of a brown adipocyte. In a further aspect, a subpopulation of CD34+cells represent the most pure human brown adipocyte progenitors known to date.

Flow cytometry, fluorescent-activated cell sorting ("FACS"), and other cell sorting techniques known in the art can be used for sorting cells obtained from various tissues and for separating BAT progenitor cells from other cells. Among other techniques known in the art, multi-color FACS can be used to identify CD31-CD34+ endothelial cells. Additionally, one or more of CD146+ pericytes, CD45+ hematopoietic cells and/or CD56+ myogenic progenitors can be separated and removed. Reverse transcriptase polymerase chain reaction ("RT-PCR") analysis can be used to confirm the absence of hematopoietic cells and myogenic progenitors from the populations of CD34+ and CD146+ cells.

Applicants have unexpectedly found that a population of progenitors is present in skeletal muscle, and that this population is, in some embodiments, found in skeletal muscle but not in white adipose tissue and, in some embodiments, exclusively found in skeletal muscle (i.e., not in other tissues). The skeletal muscle may be that of a human or of any animal, and populations of progenitor cells may be diffuse in the skeletal muscle or concentrated in discrete regions. BAT progenitor cells may, in some embodiments, be found between myofibers. Skeletal muscle BAT progenitor cells may be a stationary population or may be mobile both within skeletal muscle or other tissue and between and among different tissues. Further, BAT progenitor cells can be found in fetal, juvenile, and adult skeletal muscle.

The present teachings provide BAT progenitor cells isolated from various tissues. For example, BAT progenitor cells isolated from human skeletal muscle are provided. In some embodiments, the BAT progenitor cells are found in skeletal muscle but not in white adipose tissue, and/or are exclusively found in skeletal muscle. Some BAT progenitor cells may express UCP1, mitochondrial transcription factor A (mtTFA), and/or PPARγ coactivator-1α (PGC-1α) as well as one or more of the corresponding mRNAs. The present disclosure provides methods for detection of BAT progenitor cells and/or UCP1 mRNA in the skeletal muscle of adult humans. Although prior studies concerning UCP1 expression in adult humans have focused on white adipose tissue, applicants disclose the existence in, and isolation from, human skeletal muscle of brown adipose progenitor cells with a high potential for UCP1 expression. In some embodiments, a reservoir of BAT progenitor cells in skeletal muscle provides a mechanism for modulating energy dissipation for treatment of metabolic diseases such as obesity, diabetes, and the like.

At least a portion of the population of progenitor cells present in skeletal muscle is capable of differentiating into genuine brown adipocytes, and, in some embodiments, a portion of the population of progenitor cells present in skeletal muscle are capable of being differentiated in vitro into genuine brown adipocytes. The present disclosure provides methods for expanding BAT progenitor cell cultures and methods for differentiating BAT progenitor cells into genuine BAT cells, including methods for differentiating previously sorted cells in an adipogenic medium. In some embodiments, differentiation of sorted progenitor cells into brown adipocytes can be performed using conditions that sustain white adipocyte differentiation or by use of agents determined to promote differentiation of progenitors into brown adipocytes.

Some embodiments utilize the presence of UCP1, FABP4 (aP2), PPARγ2, mitochondrial transcription factor A (mtTFA), and/or PPARγ coactivator-1α (PGC-1α) as well as one or more of the corresponding mRNAs, to identify BAT progenitor cells that have begun to at least partially differentiate. High metabolic rate or high levels of uncoupled respiration, glucose utilization, fatty acid oxidation, or combinations of the foregoing characteristics with each other or other characteristics, can be used to identify BAT progenitor cells that have begun to at least partially differentiate. For purposes of this disclosure, BAT progenitor cells that have begun to at least partially differentiate into brown adipocytes are referred to as "differentiated brown adipocytes."

As an example, cells determined to express the CD34 marker (i.e., CD34+ cells) can be differentiated into brown adipocytes by culturing in DMEM-Ham's F-12 medium containing 0.86 μM insulin, 10 μg/ml transferrin, 0.2 nM triiodothyronine, 1 μM rosiglitazone, 100 μM 3-isobutyl-1-methylxanthine, 1 μM dexamethasone and 1% penicillin-streptomycin. Other agents may also be used to promote differentiation of progenitor cells into brown adipocytes. In some embodiments, agents identified according to the teachings of this disclosure are used to promote differentiation of progenitor cells into brown adipocytes. In some embodiments, differentiated brown adipocytes exhibit high levels of UCP1 expression, high levels of uncoupled respiration, and/or high metabolic rate.

In another example, cells expressing the CD34 marker but are substantially free of the CD31 marker (i.e., CD34+ CD31− cells) can represent a purer population of BAT progenitor cells than CD34+ cells (i.e., including both CD34+CD31− cells and CD34+CD31+ cells). In certain embodiments, an adipogenic differentiation medium not containing a PPARγ agonist (e.g., rosiglitazone), called Minimal Differentiation Medium (MDM), was shown to be sufficient to induce the differentiation of at least a proportion of adipocyte progenitor cells. The composition of MDM is: DMEM/Ham's F-12 50/50 Mix (3.151 g/l, 17.5 mM D-glucose, 3.651 g/l L-glutamine) (Cellgro #10-090-CV), 5 μg/ml (0.86 μM) insulin, 10 μg/ml transferrin, 0.2 nM 3,3',5-triiodo-L-thyronine, 100 μM 3-isobutyl-1-methylxanthine, 1 μM dexamethasone, 1% penicillin-streptomycin.

The present disclosure provides methods for increasing UCP1 mRNA expression in BAT progenitor cells, differentiated brown adipocytes, or both. For example, agents such as cell-permeating cAMP derivatives and peroxisome-proliferator-activated receptor-γ (PPARγ) agonists can be used to increase UCP1 mRNA expression in BAT progenitor cells, differentiated brown adipocytes, or both. Enhanced UCP1 expression can be determined by methods known in the art, including measurement of UCP1 mRNA by quantitative RT-PCR. Exemplary primers for use in RT-PCR analysis of UCP1 mRNA are provided as SEQ ID NOS: 1-4 and 11-12.

BAT progenitor cells exposed to adipogenic media can contain higher levels of UCP1 mRNA than BAT progenitor cells that are not exposed to adipogenic media. Cyclophilin mRNA levels can serve as a normalizing value (reflecting the number of cells or the total amount of RNA) for evaluating the abundance of UCP1 mRNA in a cell. In some embodiments, UCP1 mRNA levels in BAT progenitor cells not exposed to adipogenic media are not detectable using RT-PCR while UCP1 mRNA levels in differentiated brown adipocytes is detectable and can be normalized to cyclophilin mRNA levels. As a comparative measure of UCP1 expression, UCP1 mRNA levels in differentiated brown adipocytes can be compared to UCP1 mRNA levels in cultured mouse brown adipocytes. The present disclosure provides UCP1 mRNA levels in differentiated brown adipocytes of about 25% of the UCP1 mRNA levels in cultured mouse brown adipocytes, while in other embodiments the UCP1 mRNA level is about 25±10% or from about 15% to about 30% of the UCP1 mRNA levels in cultured mouse brown adipocytes. The present disclosure contemplates UCP1 mRNA levels in differentiated brown adipocytes in a range of from about 5% to about 100% of the UCP1 mRNA levels in cultured mouse brown adipocytes. In some embodiments, the UCP1 mRNA levels can be in excess of 100% of the UCP1 mRNA levels in cultured mouse brown adipocytes.

Differentiated brown adipocytes can contain significantly higher levels of UCP1 mRNA than cells in same-species or same-individual adult skeletal muscle biopsies. In addition, the quantity of UCP1 protein in a differentiated brown adipocyte can be approximately equal to the quantity of UCP1 protein in same-species or same-individual fetal BAT. The present disclosure contemplates UCP1 mRNA levels in human differentiated brown adipocytes being approximately equivalent to UCP1 mRNA levels in human brown adipocytes in vivo. In some embodiments the UCP1 mRNA level in a human differentiated brown adipocyte can be in a range from about 1% to many times greater than UCP1 mRNA levels in human brown adipocytes in vivo.

Figure 14:
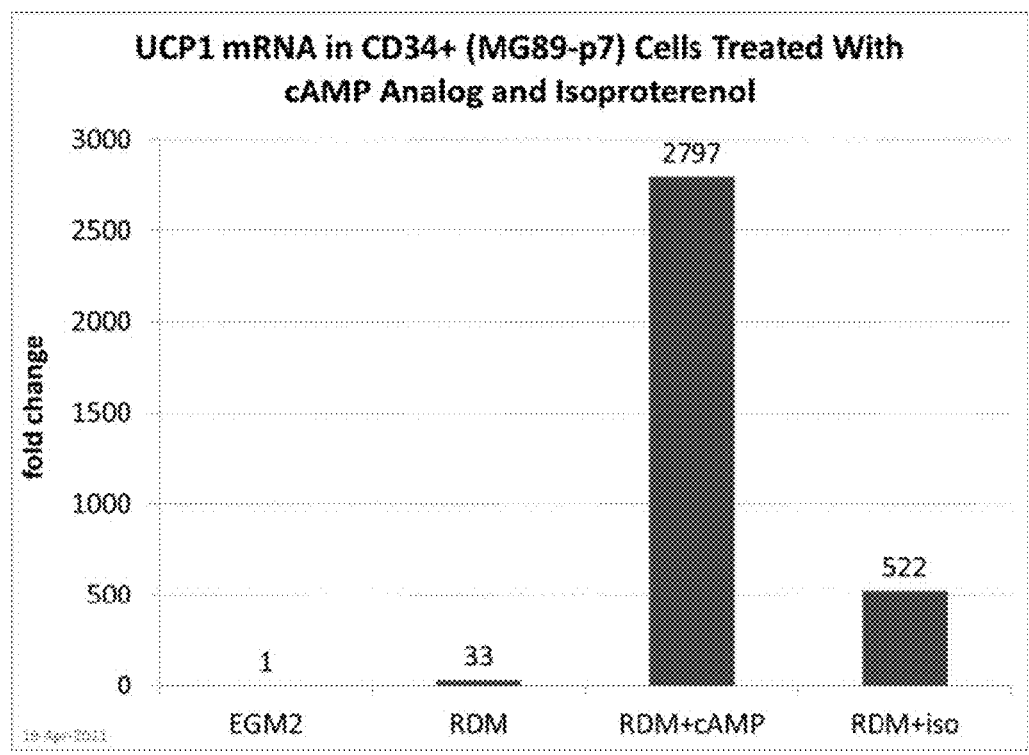
FIG. 14 shows that cAMP and β-AR agonists have synergistic effects with PPARγ agonist on UCP1 mRNA expression. RDM=Minimal Differentiation Medium+ Rosiglitazone, iso=(−)-Isoproterenol.

The present disclosure provides methods for increasing UCP1 mRNA levels in BAT progenitor cells, differentiated brown adipocytes, or both. In some embodiments, the methods provide for selectively increasing UCP1 mRNA levels in BAT progenitor cells, differentiated brown adipocytes, or both. PPARγ agonists can stimulate UCP1 mRNA production in both skeletal muscle and differentiated brown adipocytes. For example, in some embodiments, the PPARγ agonist rosiglitazone selectively stimulates UCP1 mRNA production in skeletal muscle or in differentiated brown adipocytes. Cell-permeating cAMP derivatives can stimulate UCP1 mRNA production in both skeletal muscle and in differentiated brown adipocytes. For example, in some embodiments the cell-permeating cAMP derivative 8-bromo-cAMP selectively stimulates UCP1 mRNA production in skeletal muscle or in differentiated brown adipocytes while in some embodiments the cell-permeating cAMP derivative (4-chlorophenylthio)-cAMP selectively stimulates UCP1 mRNA production in skeletal muscle or in differentiated brown adipocytes. For example, in some embodiments the combination of both the PPARγ agonist rosiglitazone and either the cell permeant cAMP analog dibutyryl-cAMP or the β-AR agonist (−)-isoproterenol can additionally selectively stimulate UCP1 mRNA production in skeletal muscle or in differentiated brown adipocytes (FIG. 14).

Figure 15:
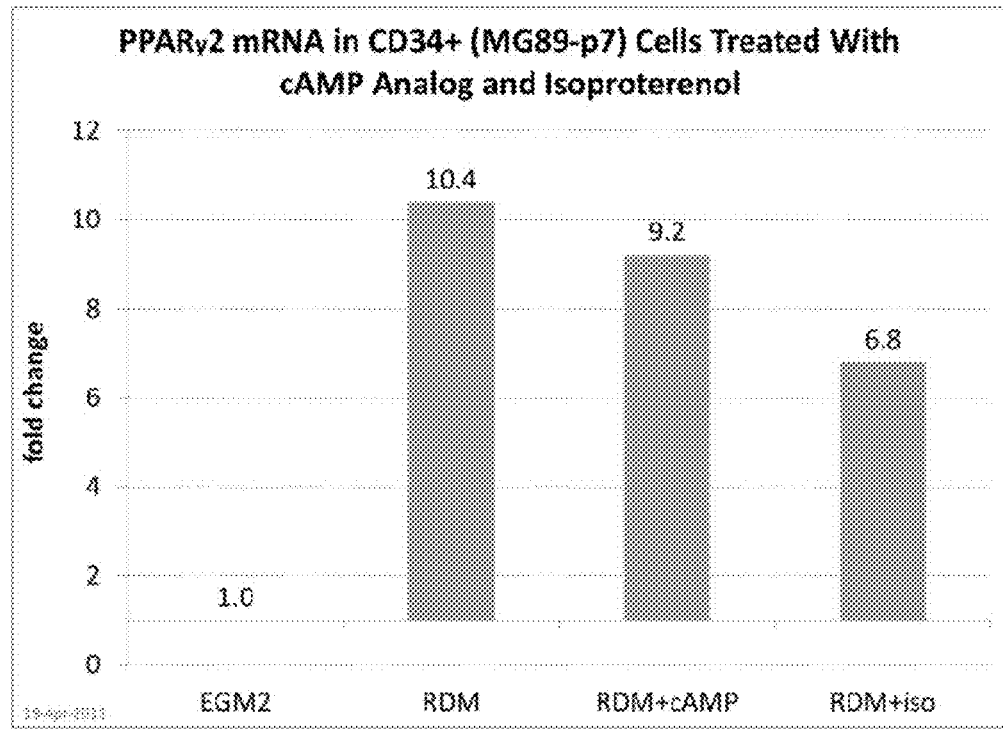
FIG. 15 shows that differentiated brown adipocytes have significantly increased levels of PPARγ2 mRNA as compared to undifferentiated BAT progenitor cells. RDM=Minimal Differentiation Medium+Rosiglitazone, iso=(−)-Isoproterenol.

Mitochondrial transcription factor A ("mtTFA") and peroxisome-proliferator-activated receptor-γ coactivator-1α ("PGC-1α") are involved in the control of mitochondriogenesis. Differentiated brown adipocytes can contain large amounts of mtTFA, PGC-1α, or both. The present disclosure provides differentiated brown adipocytes having significantly increased levels of mtTFA mRNA, PGC-1α mRNA, or both, as compared to undifferentiated BAT progenitor cells. Mitochondrial marker cytochrome oxidase IV (COX IV) is involved with the mitochondrial respiratory chain. The present disclosure provides differentiated brown adipocytes having significantly increased levels of COX IV mRNA as compared to undifferentiated BAT progenitor cells. Fatty acid binding protein-4 ("FABP4" or "aP2") and peroxisome-proliferator-activated receptor-γ2 ("PPARγ2") are genes expressed only in adipocytes (brown and white). Differentiated brown adipocytes can contain large amounts of FABP4, PPARγ2, or both. The present disclosure provides differentiated brown adipocytes having significantly increased levels of FABP4 mRNA, PPARγ2 mRNA, or both, as compared to undifferentiated BAT progenitor cells. For example, FIG. 15 shows that upon differentiation induced by RDM, RDM+cAMP or RDM+iso, PPARγ2 mRNA level increased by 10.4 fold, 9.2 fold, and 6.8 fold, respectively.

Differentiated brown adipocytes according to some embodiments have high levels of uncoupled respiration and/or high metabolic rate. Uncoupled respiration can occur when protons leak across the inner mitochondrial membrane rather than passing through the adenosine triphosphate synthase ("ATP Synthase") enzyme to drive production of adenosine triphosphate ("ATP"). The energy released by the proton movement in the electrochemical proton gradient across the membrane is dissipated as heat, rather than in the process of making ATP. Uncoupled respiration can be measured as a function of the portion of cellular respiration (e.g., oxygen consumption) that occurs independently of ATP formation by ATP Synthase. For example, oxygen consumption in the electron transport chain of oxidative phosphorylation in the presence of oligomycin, which blocks the function of ATP Synthase, provides a measure of uncoupled respiration.

The present disclosure provides differentiated brown adipocytes having significantly increased levels of uncoupled respiration as compared to undifferentiated BAT progenitor cells. In some embodiments, the present disclosure provides differentiated brown adipocytes having levels of uncoupled respiration of about 50% of total respiration. Some embodiments exhibit uncoupled respiration at levels in a range of from about 20% to about 50% of total respiration. Using the level of uncoupled respiration in adult white adipocytes as a standard for comparison, some embodiments exhibit uncoupled respiration in a range of from about 1.5 to about 3.5 times greater than in adult white adipocytes. In some embodiments, the level of uncoupled respiration is about 2.5 times greater than in adult white adipocytes. The present disclosure provides, among other things, differentiated brown adipocytes that are equipped to metabolize glucose, oxidize fatty acids, and dissipate energy as heat via uncoupling of oxidative phosphorylation.

The present disclosure provides conditions and agents (e.g., compounds, proteins, biologicals, and the like) that promote the differentiation of BAT progenitor cells to brown adipocytes, both in vitro and in vivo. In some embodiments, the differentiation-promoting agent is: a PPARγ activator, modulator, or inhibitor (e.g., rosiglitazone), a PPARα activator or modulator (e.g., clofibrate, GW9578), a PPARδ activator or modulator (e.g., GW501516 or GW0742), a dual PPARα and PPARδ activator or modulator, a pan-PPAR (α, δ, γ) activator or modulator (e.g., GW4148), a PDE1 inhibitor (e.g., vinpocetine or IBMX), a PDE3 inhibitor (e.g., siguazodan or IBMX), a PDE4 inhibitor (e.g., rolipram or IBMX), a PDE7 inhibitor (e.g., BMS 586353 or BRL 50481 or IBMX), prostaglandin J2, 9alpha,11beta-prostaglandin F2, 9beta,11alpha-prostaglandin F2, a peptide derived from the Pituitary adenylate cyclase-activating polypeptide (ADCYAP1 or PACAP) gene (PACAP propeptide, PACAP-related peptide, PACAP-38 or PACAP-27), dibutyryl-cGMP, 8 Bromo-cGMP, a NRIP1 (RIP140) inhibitor, a PTEN inhibitor (e.g., potassium bisperoxo (bipyridine) oxovanadate or dipotassium bisperoxo (5-hydroxypyridine-2-carboxyl) oxovanadate), an α1-adrenergic full or partial agonist (e.g., phenylephrine or cirazoline), an α2-adrenergic antagonist (e.g., yohimbine), an RXRα activator or modulator (e.g., LGD 1069 (Targretin) or 9-cis retinoic acid), a PGC-1α activator, a PGC-1β inhibitor or activator, adiponectin or an activator of adiponectin receptor AdipoR1 and/or AdipoR2, an NOS inhibitor or activator (e.g., 1400 W, 2-Ethyl-2-thiopseudourea or NG-nitro-L-arginine methyl ester (L-NAME) or adenosine), a Rho kinase-ROCK inhibitor (e.g., fasudil, HA1077), BDNF, a monoamine oxidase (MAO) A inhibitor and/or a MAO B inhibitor (e.g., isocarboxazid, moclobemide, selegiline), an activator of SRC, an inhibitor of EGFR (e.g., RG-14620, erlotinib or ZD1839-gefinitib or Argos protein), an inhibitor of FAAH (e.g., URB597), an inhibitor of MAPK 1 (e.g., PD98059) or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), an AMPK activator (e.g., AICAR), BMP-7, an mTOR inhibitor (e.g., rapamycin), an adenylate cyclase activator (e.g., forskolin), formoterol, salbutamol, bupropion, REV-5901, 24(S)-Hydroxycholesterol, 1,25-Dihydroxyvitamin D3, 24,25-Dihydroxyvitamin D3, Prostaglandin J2, 15 d-Prostaglandin J2, 9alpha,11beta-Prostaglandin F2, 9beta,11alpha-Prostaglandin F2, Mead acid (20:3 n-9), Docosahexaenoic acid (22:6 n-3), Docosatrienoic acid (22:3 n-3), Docosapentaenoic acid, Lysophosphatidic acid, Bongkrekic acid, 3-Bromo-7-nitroindazole, Pregnenolone 16a carbonitrile, Epibatidine, a COX-2 inhibitor (e.g., NS-398), or combinations of any of the foregoing.

In some embodiments, treatment of a subject, including a human subject, with rosiglitazone results in an increase in the production of UCP1 mRNA in the subject's skeletal muscle. Treatment of subjects with rosiglitazone can, in some embodiments, induce the appearance or differentiation of brown adipocytes in skeletal muscle, enhance expression of the UCP1 gene in existing brown adipocytes in skeletal muscle, or both. For example, in some embodiments the appearance or differentiation of brown adipocytes in skeletal muscle can be induced in a subject suffering from a metabolic disease. The brown adipocytes can provide a glucose sink with high mitochondrial and cellular respiration and fatty acid oxidation rates, dissipating energy as heat (uncoupled oxidative phosphorylation). The subject metabolic rate can be enhanced, and a decrease in body weight can be induced. Induction of the appearance or differentiation of brown adipocytes can also yield improvements in insulin sensitivity, blood glucose homeostasis and cardiovascular disease risk factors. Brown adipocytes may further secrete factors that contribute to increased insulin sensitivity and improve blood glucose homeostasis or cardiovascular health.

The present disclosure also provides assays that allow the identification of agents (e.g., compounds, proteins, biologicals, and the like) that promote the differentiation of BAT progenitor cells into brown adipocytes and/or induce the expression of the UCP1 gene in vitro, in vivo, or both. Such agents can be identified by screening compounds, proteins, biologicals, and the like. For example, in some embodiments isolated CD34+ cells can be used to screen agents for the ability to induce expression of the UCP1 gene and/or differentiation of the CD34+ cells into brown adipocytes. Agents identified in this manner can be used for a variety of research, diagnostic and therapeutic purposes, including, for example, treatment of metabolic diseases such as obesity, type 2 diabetes, insulin-resistance, dyslipidemia, and the like. In some embodiments, an agent identified by an assay according to the present disclosure is optimized for improvement of its physico-chemical and/or pharmacokinetic properties.

Expression of UCP1, FABP4 (aP2), PPARγ2, mtTFA, PGC-1α, and/or COX IV in BAT progenitor cells in vitro and in vivo can be enhanced according to methods provided in the present disclosure. In some embodiments, exposure to adipogenic media can be used to stimulate increased expression of UCP1, FABP4 (aP2), PPARγ2, mtTFA, PGC-1α, and/or COX IV in BAT progenitor cells. Agents such as a PPARγ activator, modulator or inhibitor (e.g., rosiglitazone), a PPARγ activator or modulator (e.g., clofibrate, GW9578), a PPARγ activator or modulator (e.g., GW501516 or GW0742), a dual PPARγ and PPARγ activator or modulator, a pan-PPAR (α, δ, γ) activator or modulator (e.g., GW4148), a PDE1 inhibitor (e.g., vinpocetine or IBMX), a PDE3 inhibitor (e.g., siguazodan or IBMX), a PDE4 inhibitor (e.g., rolipram or IBMX), a PDE7 inhibitor (e.g., BMS 586353 or BRL 50481 or IBMX), prostaglandin J2, 9alpha,11beta-prostaglandin F2, 9beta,11alpha-prostaglandin F2, a peptide derived from the Pituitary adenylate cyclase-activating polypeptide (ADCYAP1 or PACAP) gene (PACAP propeptide, PACAP-related peptide, PACAP-38 or PACAP-27), a NRIP1 (RIP140) inhibitor, a PTEN inhibitor (e.g., potassium bisperoxo (bipyridine) oxovanadate or dipotassium bisperoxo (5-hydroxypyridine-2-carboxyl) oxovanadate), an α1-adrenergic full or partial agonist (e.g., phenylephrine or cirazoline), an α2-adrenergic antagonist (e.g., yohimbine), an RXRα activator or modulator (e.g., LGD 1069 (Targretin) or 9-cis retinoic acid), a PGC-1α activator, a PGC-1β inhibitor or activator, adiponectin or an activator of adiponectin receptor AdipoR1 and/or AdipoR2, an NOS inhibitor or activator (e.g., 1400 W, 2-Ethyl-2-thiopseudourea or NG-nitro-L-arginine methyl ester (L-NAME) or adenosine), a Rho kinase-ROCK inhibitor (e.g., fasudil, HA1077), BDNF, a monoamine oxidase (MAO) A inhibitor and/or a MAO B inhibitor (e.g., isocarboxazid, moclobemide, selegiline), an activator of SRC, an inhibitor of EGFR (e.g., RG-14620, erlotinib or ZD1839-gefinitib or Argos protein), an inhibitor of FAAH (e.g., URB597), an inhibitor of MAPK 1 (e.g., PD98059), or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), an AMPK activator (e.g., AICAR), BMP-7, an mTOR inhibitor (e.g., rapamycin), an adenylate cyclase activator (e.g., forskolin), formoterol, salbutamol, bupropion, REV-5901, 24(S)-Hydroxycholesterol, 1,25-Dihydroxyvitamin D3, 24,25-Dihydroxyvitamin D3, Prostaglandin J2, 15 d-Prostaglandin J2, 9alpha,11beta-Prostaglandin F2, 9beta,11alpha-Prostaglandin F2, Mead acid (20:3 n-9), Docosahexaenoic acid (22:6 n-3), Docosatrienoic acid (22:3 n-3), Docosapentaenoic acid, Lysophosphatidic acid, Bongkrekic acid, 3-Bromo-7-nitroindazole, Pregnenolone 16a carbonitrile, Epibatidine, a COX-2 inhibitor (e.g., NS-398) or combinations thereof can also be used to stimulate increased expression of UCP1, FABP4 (aP2), PPARγ2, mtTFA, PGC-1α, and/or COX IV in BAT progenitor cells.

EXAMPLES

Aspects of the present teachings may be further understood in light of the following examples, which should not be construed as limiting the scope of the present teachings in any way.

Example 1: Sorting and Differentiation of Muscle Vascular Cells

In fetal skeletal muscle, CD34 and CD146 were found, by immunohistochemistry, to be expressed at the surface of endothelial cells and pericytes, respectively, although CD34 was also expressed by cells scattered in the inter-myofibrillar space. CD146+ pericytes have been found to surround CD34+ endothelial cells. A similar distribution of CD34+ and CD146+ cells was observed in adult skeletal muscle.

Vascular cells from seven independent fetal muscles (16-24 weeks of gestation) were sorted using multi-color fluorescence-activated cell sorting (FACS). Hematopoietic (CD45+) cells were first gated out, as were myogenic progenitors (CD56+). Then, endothelial cells (CD34+/CD146−) and pericytes (CD34−/CD146+) were sorted. The CD34+/CD146−/CD45−/CD56− are designated thereafter as CD34+ cells and the CD34−/CD146+/CD45−/CD56− as CD146+ cells. FIG. 1A shows CD34+/CD146− and CD34−/CD146+ cell purification. Dissociated cells were stained with PE-anti-CD34, FITC-anti-CD146, PE-Cy7-anti-CD56 and APC-Cy7-anti-CD45 antibodies and run on a FACS Aria cell sorter. Following exclusion of CD45+ and CD56+ cells (left panels), cells inside the CD34+ or CD146+ gates were isolated. The CD34+ cells amounted to 8+1% of the starting fetal muscle cell population.

Figure 1B:
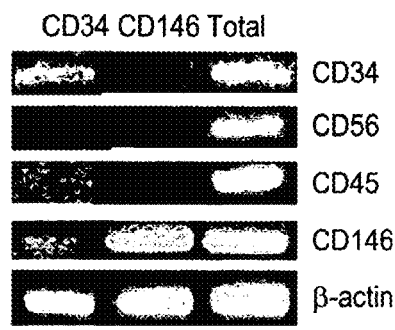

FIG. 1B shows RT-PCR analysis on CD34+/CD146−/CD45−/CD56− (CD34), CD34−/CD146+/CD45−/CD56− (CD146) and total non-sorted cells. Actin mRNA was measured as a control. The CD34+ cells were shown not to be contaminated by detectable CD45+ hematopoietic or CD56+ myogenic cells.

Figure 2A:
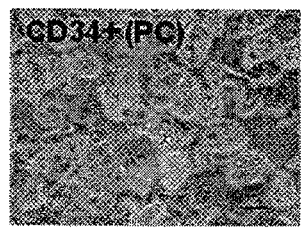
FIGS. 2A-2F show culture under adipogenic conditions of cells sorted from human fetal muscle and RT-PCR and Western blot analysis for the CD34+ cells.
Figure 2B:
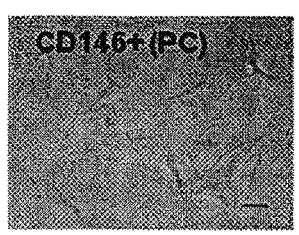
Figure 2C:
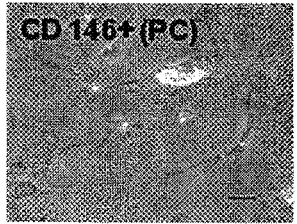
Figure 2D:
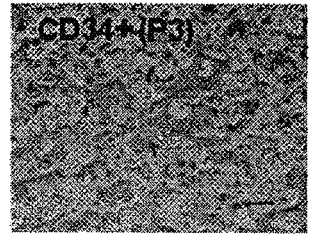

Sorted cells were grown 4-6 days in EGM2 medium and 8-12 days in the adipogenic medium described under Materials and Methods. These conditions sustain white adipocyte differentiation in WAT primary cultures. FIGS. 2A-2F show CD34+ (FIG. 2A) and CD146+ (FIG. 2B, FIG. 2C) cells in primary cultures (PC) and CD34+ (FIG. 2D) cells expanded in culture up to passage 3 (P3). Virtually all sorted fetal muscle CD34+ cells differentiated into adipocyte-like multilocular cells (FIGS. 2A, 2D). It is noteworthy that in cell culture, the multilocular structure is shared by white and brown adipocytes. In contrast, fetal muscle CD146+ cells grew very slowly under the conditions described above. They did not reach cell confluence and displayed a pericyte-like appearance characterized by a large size, spread out shape and irregular borders (FIGS. 2B and 2C). Occasional multilocular cells could be detected (FIG. 2C) The morphology of CD34+ cells expanded in culture for up to 3 passages (4 weeks) under the conditions described above was similar to that observed in primary culture, although the size of mature adipocytes was smaller (FIG. 2D).

In certain embodiments, CD45+ cells and/or CD56+ cells can be left in the CD34+/CD146− population; that is, sort CD34+/CD146− cells without first gating out at least one of CD45+ cells and CD56+ cells. It has been observed that the CD45+ and CD56+ populations can be relatively small (e.g., each population less than 5%, less than 4%, less than 3%, less than 2% or less than 1% of the total stroma-vascular cells from muscle). Therefore, a relatively pure brown adipocyte progenitor population can be isolated without the need to gate out at least one of CD45+ and CD56+ populations. Furthermore, CD45+ cells are hematopoietic progenitors and do not grow or differentiate significantly in the adipogenic media. CD56+ cells are muscle precursors and do not grow or differentiate significantly in the adipogenic media. Thus, the presence of CD45+ cells and/or CD56+ cells do not significantly affect the proliferation and/or differentiation of the CD34+ cells.

Example 2: UCP1 Expression in Cultivated CD34+ Cells

Figure 2E:
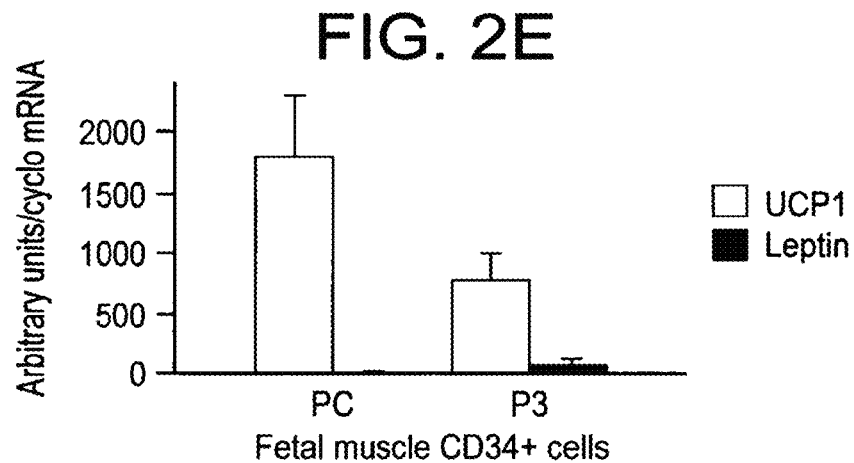

The remarkable adipocyte-like differentiation of fetal muscle CD34+ cells was an incentive for further characterization. Strikingly, quantitative RT-PCR revealed a high level of UCP1 mRNA in these cells. FIG. 2E shows quantitative RT-PCR determination of UCP1 (empty columns) and leptin (gray columns) mRNA expression in CD34+ cells in primary culture (PC) or expanded up to passage 3 (P3). The mean UCP1 mRNA level normalized to cyclophilin A was 1797±510 arbitrary units (i.e., ±s.e.m. of arbitrary values normalized using the corresponding cyclophilin A values; n=4-7), corresponding to a cycle threshold (Ct) of 22 for 25 ng of cDNA in the assay.

For comparison, the mean UCP1 mRNA level normalized to cyclophilin A in mouse brown adipocytes differentiated in culture was 7715±2649 (n=10) arbitrary units. Therefore, the level of UCP1 mRNA in human CD34+ cells amounted to almost one fourth of that in mouse brown adipocytes in culture. Human fetal BAT was not used as a positive control for quantitative RT-PCR analysis because the risk of RNA degradation was high due to the time elapsed after the termination of the pregnancy. The amplicon was cloned and sequenced and found to be 100% identical to human UCP1. In fetal muscle CD34+ cells expanded up to passage 3 a high UCP1 mRNA expression, amounting to 43% of that detected in primary cultured cells, was still observed. UCP1 mRNA expression was not detected in non-differentiated fetal muscle CD34+ cells or in CD146+ cells in primary culture. The level of leptin mRNA was 9.9±5.5 and 71±52 arbitrary units in primary cultured and expanded cells, respectively (FIG. 2E).

Example 3: Additional Phenotyping of the CD34+ Cells

To better characterize the gene expression pattern of the fetal muscle CD34+ cells expanded in culture a gene chip analysis was performed. The levels of expression of several representative gene mRNAs with significant Detection P-Values (p<0.01) are shown in Table 1 and compared with those in human muscle biopsies. The following protein mRNAs were chosen: UCP1 as a reference gene, mitochondrial transcription factor A (mtTFA) and peroxisome-proliferator-activated receptor (PPARγ) and PPARγ coactivator-1α (PGC-1α), which are involved in the control of thermogenesis and mitochondriogenesis, enzymes of the mitochondrial respiratory chain succinate dehydrogenase (SDH) and cytochrome oxidase IV (COX IV), enzymes of the fatty acid degradation pathway, carnitine palmitoyltransferase IB (CPT1B), acyl-CoenzymeA dehydrogenases long chain (ACAD) and C-4 to C-12 straight chain (ACADM), and the skeletal muscle markers myogenin, myogenic factor 5 (Myf5) and myogenic differentiation 1 (MyoD1). Cidea, which is highly expressed in BAT and may act as a suppressor of UCP1 activity [16], was chosen as a BAT marker. The Genbank accession numbers of these genes are shown in the supplemental data.

TABLE 1

| mRNA | Accession No. | CD34+ cells | Human muscle biopsies |
| --- | --- | --- | --- |
| UCP1 | NM_021833 | 94 | n.s. |
| mTFA | NM_003201.1 | 413 | 205 |
| PPARγ | NM_138712.2 | 3326 | 84 |
| PGC-1α | NM_013261.2 | 137 | 619 |
| COX IV | NM_001861.2 | 13*082 | 13*407 |
| SDH | NM_003000.1 | 2390 | 5187 |
| CPTIB | NM_004377.2 | 99 | 639 |
| ACAD | NM_032169.3 | 1032 | 141 |
| ACADM | NM_000016.2 | 599 | 1640 |
| Myogenin | NM_002479.3 | n.s. | 267 |
| Myf5 | NM_05593 | n.s. | 21 |
| MyoD1 | NM_002478 | n.s. | 12 |
| Cidea | NM_198289.1 | 337 | n.s. |

The data in Table 1 are expressed as the average Illumina signal. The Detection P-Values are <0.01. The following abbreviations are used: n.s., not significant; mtTFA, mitochondrial transcription factor A; PPARγ, peroxisome-proliferator-activated receptor-γ; PGC-1α, PPARγ coactivator-1α; COX IV, cytochrome oxidase IV; SDH, succinate dehydrogenase; CPT1B, carnitine palmitoyltransferase IB; ACAD, acyl-CoenzymeA dehydrogenases long chain; ACADM, C-4 to C-12 straight chain; Myf5, myogenic factor 5; MyoD1, myogenic differentiation 1.

UCP1 was significantly expressed in fetal muscle-expanded CD34+ cells but not in adult muscle biopsies (for which p=0.12). The levels of mRNA expression of the selected genes in expanded CD34+ cells from fetal muscle were comparable with those of the adult muscle biopsies with the exceptions of PGC-1α and CPT1B mRNAs (which were about 5-fold less expressed in the cells) and of the PPARγ and ACAD mRNAs (which were 40- and 7-fold less expressed, respectively in the muscle biopsies). The muscle markers myogenin, Myf5 and MyoD1 mRNA were significantly expressed in the muscle but not in the cells whereas the BAT marker Cidea mRNA was expressed in the cells but not in the muscle. No β3-adrenoceptor mRNA could be detected in the gene chip analysis. It is noteworthy, however, that β3-adrenoceptor mRNA was detected by quantitative RT-PCR (arbitrary value 0.084±0.044 with cyclophilin A as a reference; n=4) in fetal muscle CD34+ cells in primary culture. Measurements of mtTFA, PGC-1α and COX IV were also performed by quantitative RT-PCR to confirm the gene chip data with a different technique. The results were confirmatory, showing that fetal muscle CD34+ cells in primary culture express high levels of mtTFA, PGC-1α and COX IV mRNA [amounting to 306±117, 385±294, and 23,400±10,300 arbitrary units (n=3-4), respectively], using cyclophilin A as a reference.

Figure 2F:
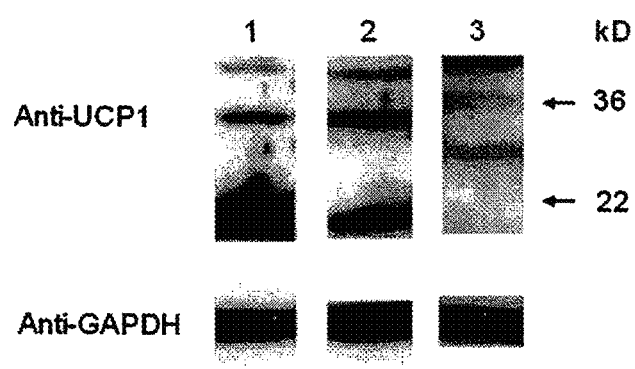

The UCP1 protein, as assessed by Western blotting with an anti-mouse antibody cross-reacting with human UCP1 (80% identity), was as abundant in primary cultured fetal muscle CD34+ cells as in fetal BAT. FIG. 2(F) shows representative Western blot analysis of UCP1 and glyceraldehyde phosphate dehydrogenase (GAPDH) proteins in tissue or whole cell extracts. Interscapular BAT of a 19-week fetus (Lane 1), CD34+ cells in primary culture (Lane 2), and skeletal muscle of an adult human (Lane 3) are shown. 25 µg of protein was loaded into each lane.

Example 4: Uncoupling of Oxidative Phosphorylation

To get insight into the possible function of UCP1 in muscle-derived cells, mitochondrial respiration of isolated cultured human fetal muscle CD34+ cells and human adult white adipocytes was compared. Basal respiration was defined as the antimycin A-sensitive oxygen consumption. Uncoupled respiration (proton leak) was defined as the percentage of basal respiration insensitive to the ATP synthase blocker oligomycin.

Figure 3A:
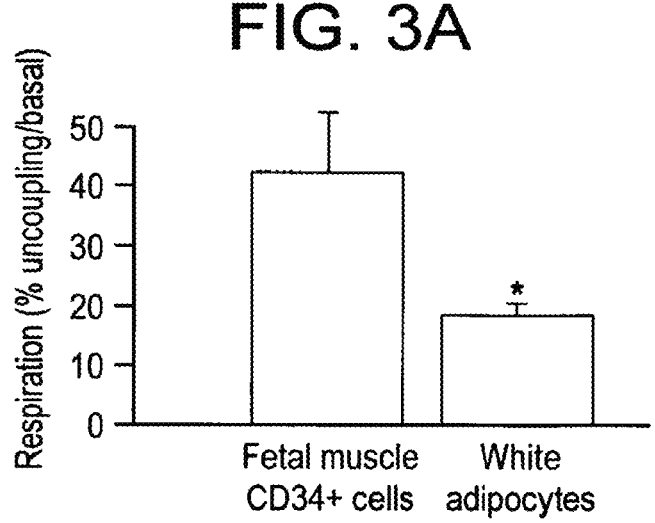
FIGS. 3A-3C show uncoupling of mitochondrial respiration and control of UCP1 mRNA expression in human fetal muscle CD34+ cells.

FIG. 3A shows uncoupling of mitochondrial respiration in isolated fetal muscle CD34+ cells and in human adult white adipocytes grown in primary culture and freshly trypsinized. The results are means s.e.m; * p<0.05. n=3. The ratios of uncoupled to total respiration were 47±12% and 19±2% in human fetal muscle CD34+ cells and adult white adipocytes, respectively.

FIG. 16 shows that the CD31− cells, upon differentiation into brown adipocytes, display more highly uncoupled respiration and greater respiration capacity compared to the same cells prior to differentiation.

Example 5: Modulation of UCP1 Expression in Cultured CD34+ Cells

Figure 3B:
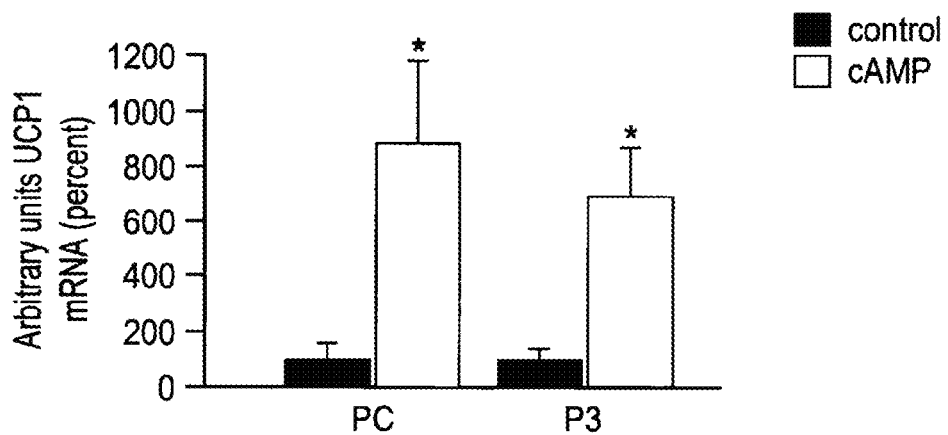

UCP1 mRNA expression in fetal muscle CD34+ cells could be modulated by drug treatment. Cell-permeating cAMP derivatives strongly stimulated (7 to 8-fold) UCP1 mRNA expression in both primary cultured and expanded cells. The effects of cAMP derivatives, 8-bromo-cAMP, 0.25 mM or (4-chlorophenylthio)-cAMP, 0.25 mM (cAMP) on UCP1 mRNA expression in CD34+ cells in primary culture (PC) or expanded up to passage 3 (P3) are shown in FIG. 3B. All the cells were grown for 4-6 days in EGM2 medium and then placed for 8-12 days in the adipogenic medium described under Materials and Methods. The results are means±s.e.m. of arbitrary values normalized using the corresponding cyclophilin A values. They are expressed in % of their respective untreated (control) values considered as 100% (* p<0.05, n=3-6).

Figure 3C:
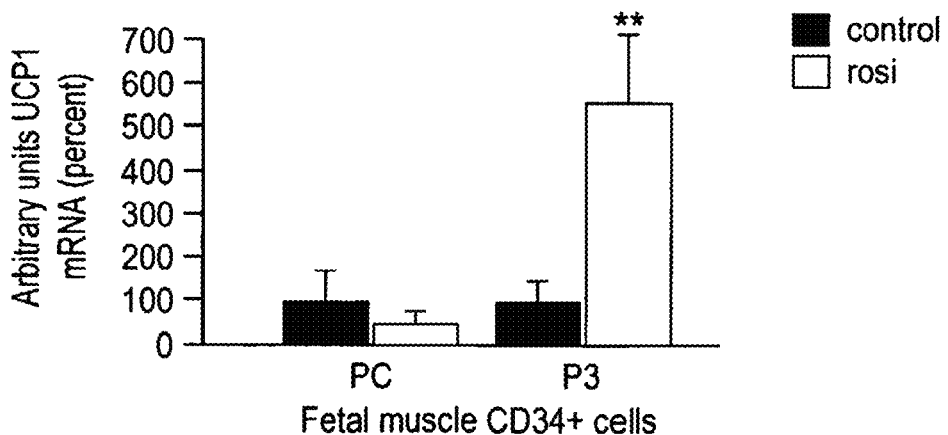

Rosiglitazone, a PPARγ agonist, had no effect in primary culture cells but strongly stimulated (8-fold) UCP1 mRNA expression in expanded cells. The effects of rosiglitazone (Rosi) 1 µM on UCP1 mRNA expression in CD34+ cell PC or P3 are shown in FIG. 3C. The results are expressed as in FIG. 3B (**p<0.01, n=4-7).

Example 6: Muscle Specificity and Persistence Throughout Life of Human Brown Adipocyte Progenitors The derivation of UCP1-expressing cells from human fetal muscle raised the question of the restriction of brown adipocyte progenitors to this tissue and to the fetal stage. To address this issue, CD34+ cells purified by FACS from human fetal pancreas, lung and liver were cultured under the same adipogenic conditions as fetal muscle CD34+ cells. The sorted cells grew slowly and only a small proportion of them became multilocular. UCP1 mRNA was not expressed in pancreas or lung cells; however, a minor expression was measured in liver cells, which amounted to 2% of that detected in fetal muscle CD34+ cells (not shown).

Figure 4A:
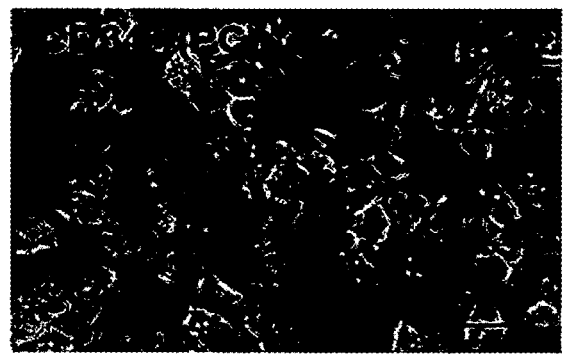
FIGS. 4A-4C show characterization of adult muscle and WAT cells in adipogenic culture.
Figure 4B:
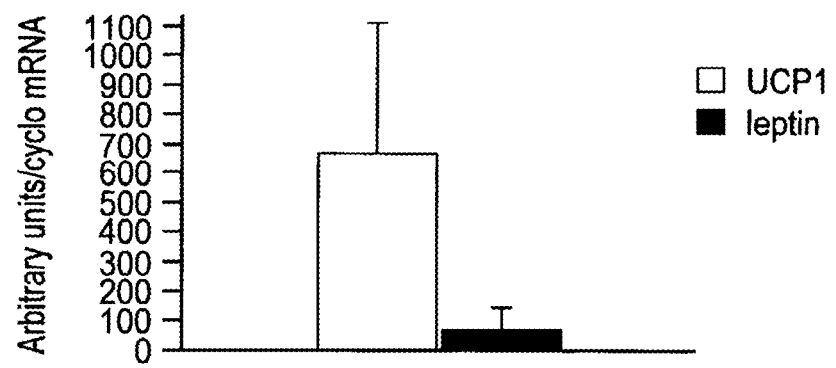
Figure 4C:
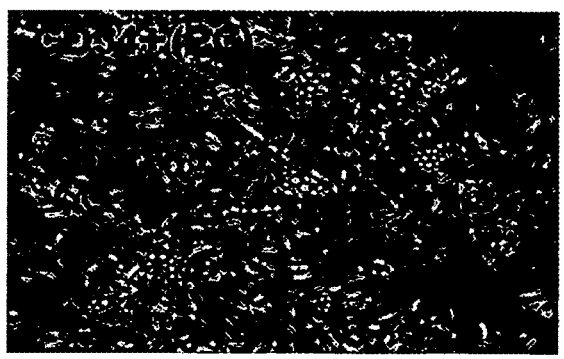

CD34+ cells sorted from 4 adult (50-78 years) human skeletal muscle samples, grown in primary culture (PC) under adipogenic conditions, also differentiated into multilocular cells. These cells were interspersed with other types of cells, some of them containing small lipid droplets (FIG. 4A). The level of UCP1 mRNA (370±132 arbitrary units) was 21% of that detected in primary cultured fetal muscle CD34+ cells. In contrast, leptin expression (75±69 arbitrary units) was 7.6-fold higher than in fetal cells. FIG. 4B shows quantitative RT-PCR determination of UCP1 (empty column) and leptin (gray column) mRNA expression. All the cells were grown for 4-6 days in EGM2 medium and then placed for 8-12 days in the adipogenic medium described under Materials and Methods. The results are the mean±s.e.m. of arbitrary values normalized to the corresponding cyclophilin A values (n=4-5). CD34+ cells sorted from 4 adult (45-55 years) human WAT samples were also grown in primary culture (PC) under adipogenic conditions. They became partially multilocular (FIG. 4C), but did not express UCP1 mRNA.

Example 7: Detection of UCP1 mRNA Expression in Human Muscle and Effect of Rosiglitazone In Vivo Brown adipocyte progenitors of adult human skeletal muscle can differentiate in vivo and give rise to UCP1 expressing cells. The presence of UCP1 mRNA in the adult human skeletal muscle was tracked using a high sensitivity RT-PCR technique and, in fact, low levels of UCP1 mRNA were detected in the rectus abdominus muscle of 10 lean subjects (UCP1/cyclophilinA ratio: 24±9). The PCR-amplified fragment was sequenced and found to be 100% identical to human UCP1. The UCP1 mRNA level in adult human muscle was 75-fold lower than that in fetal muscle CD34+ cells in culture.

Since the PPARγ agonist rosiglitazone was a strong inducer of UCP1 mRNA expression in muscle CD34+ cells in culture, the effect of this compound in vivo in humans was investigated. Vastus lateralis muscle biopsies from 7 obese patients with type 2 diabetes mellitus treated for the management of their metabolic syndrome with rosiglitazone were used. The biopsies were obtained before and after 8 weeks of treatment with rosiglitazone (2×4 mg per day). The treatment with rosiglitazone resulted in a significant improvement of the patients' insulin resistance and diabetes. In that study rosiglitazone, concomitantly with the improvement in insulin sensitivity, increased the level of expression of UCP1 in muscle by about 1.6-fold. FIG. 5 shows the quantitative RT-PCR determination of UCP1 mRNA expression. The results are the means±s.e.m. of arbitrary values normalized using the corresponding cyclophilin A values (n=7, *p<0.05 vs. control). Since the RT-PCR conditions used were different, the arbitrary values of this figure do not provide a direct comparison to those of FIGS. 2A-4C.

In FIG. 5, showing UCP1 mRNA levels in skeletal muscle biopsies from a patient group (n=7), "control" corresponds to levels before treatment, and "Rosi" corresponds to levels after treatment (8 weeks) with rosiglitazone. Being a longitudinal study the effect of rosiglitazone on UCP1 levels in each individual (comparison of individual values for the "control"-before and "Rosi"-after conditions) were determined. Starting with 25 ng cDNA (produced by reverse transcription of RNA) the threshold of detection (Ct) during real-time PCR was about 22 for UCP1 and about 18 for cyclophilin. The effect of rosiglitazone (UCP1 level at end of treatment vs. before treatment) were as follows:

Patient 1: 50% increase (to 150%, control=437, Rosi=652 arbitrary units)
Patient 2: no change (to 100%, control=444, Rosi=453 arbitrary units)
Patient 3: 80% increase (to 180%, control=378, Rosi=677 arbitrary units)
Patient 4: 180% increase (to 280%, control=260, Rosi=730 arbitrary units)
Patient 5: 8% increase (to 108%, control=553, Rosi=600 arbitrary units)
Patient 6: 310% increase (to 410%, control=135, Rosi=556 arbitrary units)
Patient 7: 10% increase (to 110%, control=128, Rosi=142 arbitrary units)

Strong effects of rosiglitazone, varying between 1.5- and 4.1-fold, were observed in 4 out 7 patients. This result suggests that rosiglitazone induced the appearance of brown adipocytes and/or enhanced the expression of the UCP1 gene in existing brown adipocytes in the skeletal muscle of the patients. This effect of the PPARγ agonist may play a key role in the therapeutic effect of this agent as an insulin-sensitizer.

Example 8: Screening of Potential Modulators of the Human UCP1 Promoter/Enhancer Region The identified and isolated CD34+cells can be used as a tool to identify agents (compounds, proteins, biologicals, and the like) that induce the differentiation of these cells into brown adipocytes or modulate the expression of UCP1. For example, an RT-PCR based approach can be used to measure UCP1 mRNA levels which may be affected by certain agents. Alternatively, using a tagged UCP1 protein as marker, immunohistochemistry (e.g., fluorescence) can be used to detect changes in UCP1 protein level to screen for agents that modulate UCP1 expression.

For this purpose and by way of example, a large region (6 kb) of DNA upstream (in 5') of the transcription start site of the human UCP1 gene (containing the promoter/enhancer region) has been cloned into a reporter/MAR GFP (Green Fluorescent Protein) or luciferase. This construct has been used to transfect CD34+ cells, and the cells grown in multiwell plates and screened for agents that increase the fluorescence (GFP) or luminescence (luciferase) of the cells, reflecting induction of gene expression (and thus increased UCP1 expression). This allows the identification of agents that can enhance the differentiation of CD34+ cells into brown adipocytes and/or the expression of UCP1 by enhancing the transcription of the UCP1 gene and/or by enhancing the translation of the UCP1 transcript, and/or by stabilizing the UCP1 transcript or protein.

For example, a PPARγ modulator or activator like rosiglitazone can be used to promote the differentiation of CD34+ progenitor cells into brown adipocytes (FIGS. 3C and 5). Another example is the use of cAMP derivatives like, 8-bromo-cAMP and/or (4-chlorophenylthio)-cAMP (FIG. 3B) or protein kinase A (PKA) activators or phosphodiesterase inhibitors. Another example is the use of triiodothyronine (T3), other thyroid hormones, agonists or modulators of the thyroid hormone receptors TRa and/or TRβ. Another example is to use β-adrenergic agonists like isoproterenol (pan-agonist) or specific β1-, β2-, β3-agonists or modulators, either alone or in combination with a PPARγ modulator or activator like rosiglitazone. Another is the use of modulators of the candidate receptors revealed by gene chip studies or of target genes in the signaling pathway downstream these receptors.

Example 9: Gene Chip Studies

Gene chip studies were performed to identify molecular pathways that play a role in the differentiation of CD34+ progenitor cells into brown adipocytes and/or the induction of the expression of UCP1. CD34+ cells were isolated from human skeletal muscle biopsies, and were used in two studies: (1) cAMP study: CD34+ cells were differentiated as described in Materials and Methods (Control) plus addition of vehicle (Control 1 sample) or cAMP (cAMP sample); and (2) Rosiglitazone study: CD34+ cells were differentiated as described in Materials except that rosiglitazone was omitted from the adipogenic medium (Control 2 sample). Rosiglitazone was added only to the second sample (Rosiglitazone sample) in this study. As discussed above, these compounds have been shown to promote the differentiation of CD34+ cells into brown adipocytes and the expression of UCP1 (see FIGS. 3B and 3C).

Total RNA was purified from these samples, and transcriptional profiles were assessed with Illumina Human WG-6 BeadChip (Expression Analysis, Inc., Durham, N.C.). Results were analyzed with Ingenuity Pathway Analysis 7.0 (trial version). These results were used to determine what molecular pathways are involved in the differentiation of CD34+ cells into brown adipocytes, and, more importantly, what molecular targets can be used for the development of agents that promote the appearance of brown adipocytes and the expression of UCP1.

This work showed that the following actions/agents should promote brown adipocyte development: a PPARγ activator, modulator or inhibitor (e.g., rosiglitazone), a PPARα activator or modulator (e.g., clofibrate, GW9578), a PPARδ activator or modulator (e.g., GW501516 or GW0742), a dual PPARα and PPARδ activator or modulator, a pan-PPAR (α, δ, γ) activator or modulator (e.g., GW4148), a PDE1 inhibitor (e.g., vinpocetine or IBMX), a PDE3 inhibitor (e.g., siguazodan or IBMX), a PDE4 inhibitor (e.g., rolipram or IBMX), a PDE7 inhibitor (e.g., BMS 586353 or BRL 50481 or IBMX), prostaglandin J2, 9alpha,11beta-prostaglandin F2, 9beta,11alpha-prostaglandin F2, a peptide derived from the Pituitary adenylate cyclase-activating polypeptide (ADCYAP1 or PACAP) gene (PACAP propeptide, PACAP-related peptide, PACAP-38 or PACAP-27), a NRIP1 (RIP140) inhibitor, a PTEN inhibitor (e.g., potassium bisperoxo (bipyridine) oxovanadate or dipotassium bisperoxo (5-hydroxypyridine-2-carboxyl) oxovanadate), an α1-adrenergic full or partial agonist (e.g., phenylephrine or cirazoline), an α2-adrenergic antagonist (e.g., yohimbine), an RXRα activator or modulator (e.g., LGD 1069 (Targretin) or 9-cis retinoic acid), a PGC-1α activator, a PGC-1β inhibitor or activator, adiponectin or an activator of adiponectin receptor AdipoR1 and/or AdipoR2, an NOS inhibitor or activator (e.g., 1400 W, 2-Ethyl-2-thiopseudourea or NG-nitro-L-arginine methyl ester (L-NAME) or adenosine), a Rho kinase-ROCK inhibitor (e.g., fasudil, HA1077), BDNF, a monoamine oxidase (MAO) A inhibitor and/or a MAO B inhibitor (e.g., isocarboxazid, moclobemide, selegiline), an activator of SRC, an inhibitor of EGFR (e.g., RG-14620, erlotinib or ZD1839-gefinitib or Argos protein), an inhibitor of FAAH (e.g., URB597), an inhibitor of MAPK 1 (e.g., PD98059), or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), an AMPK activator (e.g., AICAR), BMP-7, an mTOR inhibitor (e.g., rapamycin), an adenylate cyclase activator (e.g., forskolin), formoterol, salbutamol, bupropion, REV-5901, 24(S)-Hydroxycholesterol, 1,25-Dihydroxyvitamin D3, 24,25-Dihydroxyvitamin D3, Prostaglandin J2, 15d-Prostaglandin J2, 9alpha,11beta-Prostaglandin F2, 9beta,11alpha-Prostaglandin F2, Mead acid (20:3 n-9), Docosahexaenoic acid (22:6 n-3), Docosatrienoic acid (22:3 n-3), Docosapentaenoic acid, Lysophosphatidic acid, Bongkrekic acid, 3-Bromo-7-nitroindazole, Pregnenolone 16a carbonitrile, Epibatidine, a COX-2 inhibitor (e.g., NS-398) or combinations of any of the foregoing.

Example 10: Sorting of Muscle Vascular Cells Using CD31 as an Additional Marker

With the aim of further purifying the CD34+ cells in search for the purest physiological brown adipocyte progenitors, stroma-vascular cells were purified from two independent samples of human fetal skeletal muscle (18-19 weeks of gestation). Following the CD45, CD56, CD34, and CD146 sorting described above, an additional step of FACS sorting using an anti-CD31 antibody was performed. The cells were sorted based on the presence of the mature endothelial cell surface marker CD31 (CD31+) or absence of that marker (CD31-). It was hypothesized that the CD31- subpopulation may be a purer progenitor of human brown adipocytes. The CD31- cell fraction amounted to about 80% of the CD34+ cell population derived from skeletal muscle. For purpose of simplicity, CD34+/CD45-/CD56-/CD146-/CD31- are called "CD31-" cells [EMC309 (CD31-) and EMC314 (CD31-)]. CD34+/CD45-/CD56-/CD146-/CD31+ are called "CD31+" cells [EMC309 (CD31+) and EMC314 (CD31+)]. In addition, the myogenic progenitor cells expressing the cell surface antigen CD56 (CD56+) were also sorted and cultured: CD34+/CD45-/CD56+ (from EMC314) and CD45-/CD56+ (from EMC309) are called "CD56+" cells [EMC309 (CD56+) and EMC314 (CD56+)].

The sorted cells (CD31-, CD31+, and CD56+ cell populations) were grown under the same conditions as described above, i.e., 2-4 days in proliferation medium (EGM2) and 10-16 days in adipogenic differentiation medium. Micrographs of the isolated cells in culture in EGM2 medium before expansion are shown in FIGS. 6A-8B.

The capability of the CD31-, CD31+, and CD56+ cell populations to differentiate into adipocytes was first tested in adipogenic differentiation medium in the absence of rosiglitazone. An adipogenic differentiation medium not containing a PPARγ agonist (e.g., rosiglitazone), called Minimal Differentiation Medium (MDM), was shown to be sufficient to induce the differentiation of at least a proportion of adipocyte progenitor cells. The composition of MDM is: DMEM/Ham's F-12 50/50 Mix (3.151 g/l, 17.5 mM D-glucose, 3.651 g/l L-glutamine) (Cellgro #10-090-CV), 5 µg/ml (0.86 µM) insulin, 10 µg/ml transferrin, 0.2 nM 3,3',5-triiodo-L-thyronine, 100 µM 3-isobutyl-1-methylxanthine, 1 µM dexamethasone, 1% penicillin-streptomycin.

An appreciable fraction (approximately 20%) of the CD31- cells differentiated into adipocyte-like multilocular cells when exposed to Minimal Differentiation Medium (FIG. 9B for EMC309, FIG. 9F for EMC314), and virtually all the CD31- cells differentiated into adipocyte-like multilocular cells when exposed to MDM containing a brown adipocyte-promoting compound such as the PPARγ activator rosiglitazone or BMP7 [26-28] (FIG. 9C-D, 9G-H).

It was also found that the addition of a PPARγ agonist (e.g., rosiglitazone at 1 microM) either from the onset of differentiation (day 0) or, instead, for 2-3 days only starting 2 or 3 days before the induction of differentiation (from day -3 or -2 to day 0) strongly promoted the differentiation of the CD31-cells into brown adipocytes. Similarly, addition of bone morphogenic protein-7 (BMP7 at 6 nM) before the induction of differentiation (from day -3 or -2 to day 0) strongly promoted the differentiation of the CD31-cells into brown adipocytes.

In contrast, the CD31+ cells (FIGS. 10A-10H) and the CD56+ (FIGS. 11A-11H) cells did not grow well in MDM, and did not differentiate into adipocyte-like multilocular cells under the conditions described above, with or without rosiglitazone or BMP7.

Figure 12A:
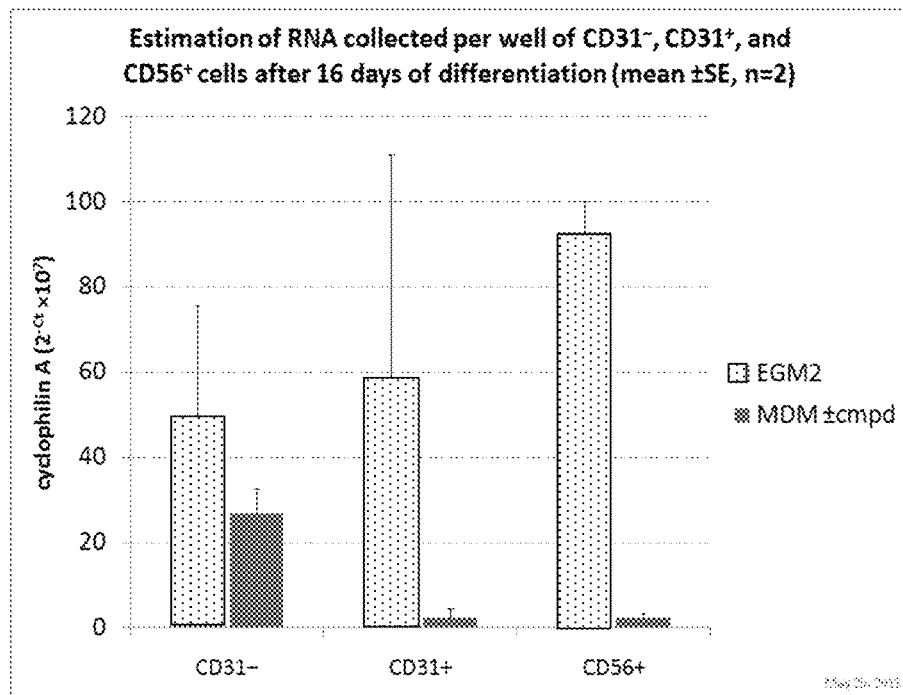
FIGS. 12A-12B show that significantly less RNA (reflecting a lower number of cells) was recovered from the CD31+ and CD56+ cells than from the CD31− cells grown in adipogenic differentiation medium (MDM), irrespective of the presence or absence of rosiglitazone or BMP7 (+/− cmpd). Compare dark bars (MDM+/−cmpd) in CD31− samples vs. CD31+ and CD56+ samples.
Figure 12B:
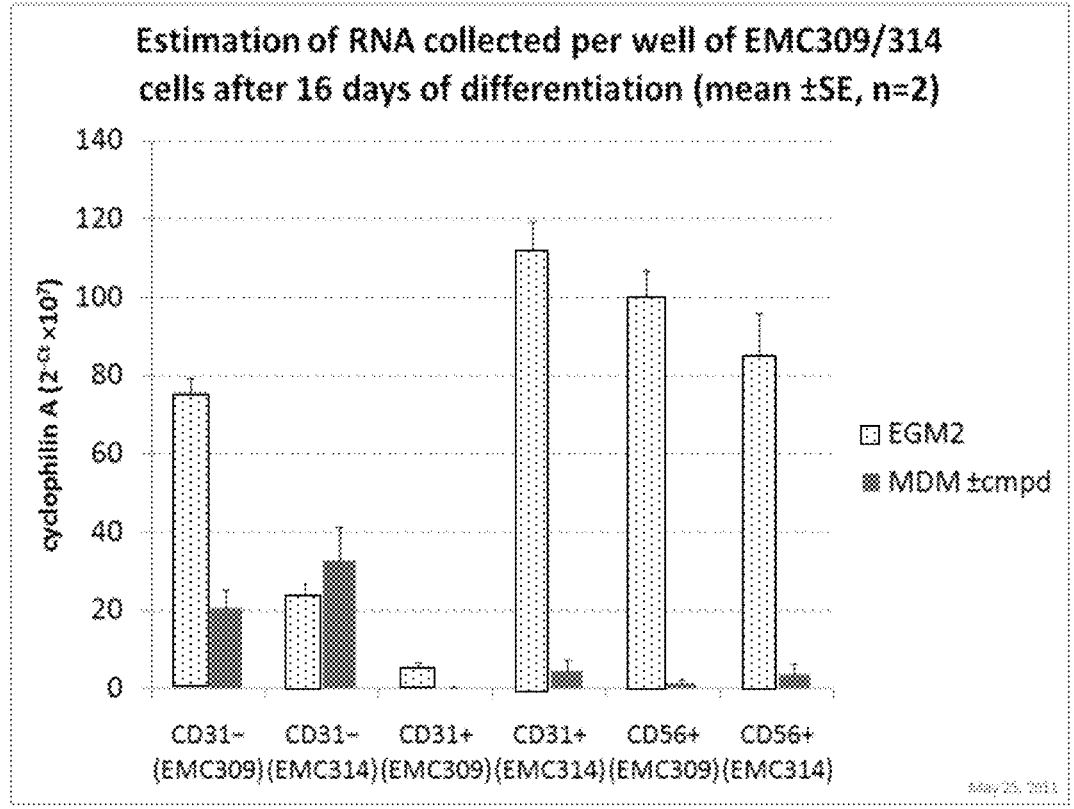

All cell populations (CD31-, CD31+ and CD56+) grew well in proliferation medium (EGM2) over the whole 12-20 day study (FIGS. 9A and 9E for CD31-, FIGS. 10A and 10E for CD31+, FIGS. 11A and 11E for CD56+) but only the CD31- cells grew without detaching in MDM with or without rosiglitazone or BMP7. The difference in cell density at day 14-16 between the CD31- and the CD31+ or CD56+ cells when grown in MDM is illustrated in the micrographs in FIGS. 9-11 (compare FIG. 9B, 9F to FIG. 10B, 10F or FIG. 11B, 11F; FIG. 9C, 9G to FIG. 10C, 10G or FIG. 11C, 11G; FIG. 9D, 9H to FIG. 10D, 10H or FIG. 11D, 11H) as well as in the amount of cyclophilin mRNA (reflecting the number of cells) measured in the cultured cells at day 16 (FIG. 12A and FIG. 12B).

In certain embodiments, CD45+ cells and/or CD56+ cells can be left in the CD31-/CD34+/CD146- population; that is, sort CD31-/CD34+/CD146- cells without first gating out at least one of CD45+ cells and CD56+ cells. As discussed above, the CD45+ and CD56+ populations can be relatively small (e.g., each population less than 5%, less than 4%, less than 3%, less than 2% or less than 1% of the total stroma-vascular cells from muscle), and do not grow or differentiate significantly in the adipogenic media. Therefore, a relatively pure brown adipocyte progenitor population can be isolated without the need to gate out at least one of CD45+ and CD56+ populations. Furthermore, the presence of CD45+ cells and/or CD56+ cells do not significantly affect the proliferation and/or differentiation of the CD34+ cells.

Example 11: UCP1 Expression in Cultured CD31−, CD31+ and CD56+ Cells

Quantitative RT-PCR revealed a high level of UCP1 mRNA in the differentiated CD31− cells (normalized with cyclophilin A mRNA). As compared to the EGM2 control condition the levels of UCP1 expression were increased by 10-21-fold in MDM, 507-553-fold with rosiglitazone, and 78-127-fold with BMP7 (FIG. 13).

The proportion of differentiated (adipocyte) cells as well as the expression of UCP1 was highly increased by addition of either: (a) 1 microM rosiglitazone (a PPARγ agonist) to the MDM starting at day 0 (MDM+rosi) (FIG. 13), or (b) 6 nM BMP7 (Bone Morphogenic Protein-7) only in the proliferation medium (EGM2) two or three days before induction of differentiation, i.e., from day −2 or day −3 to day 0 (FIG. 13).

Figure 13:
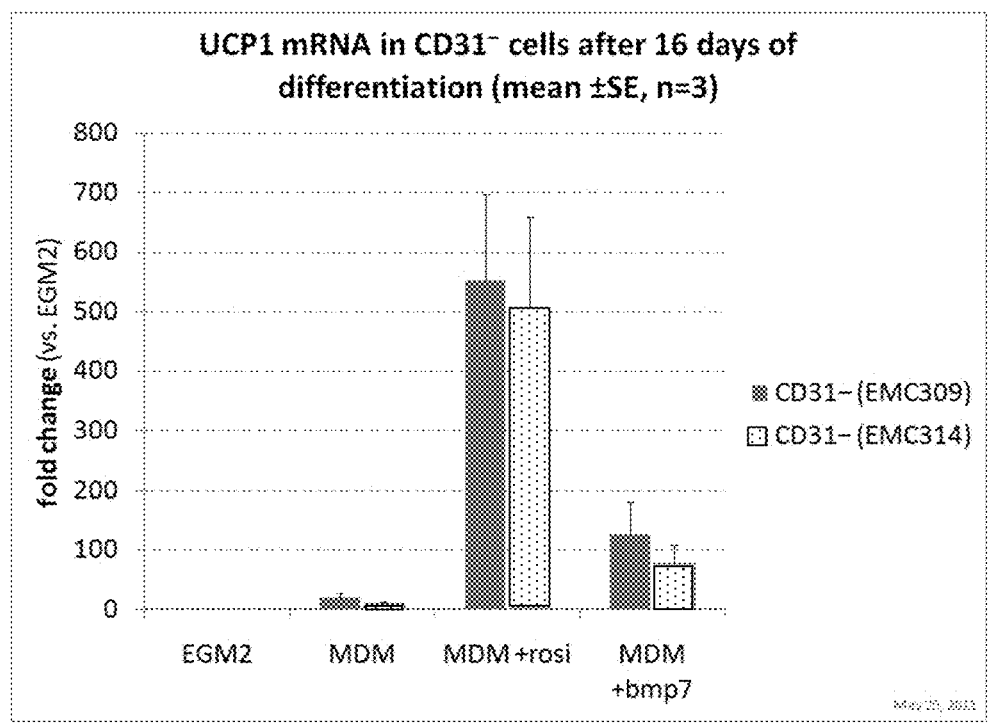
FIG. 13 shows that CD31− cells differentiate into adipocytes and express UCP1. Exposure of CD31− cells to rosiglitazone or BMP7 robustly increases the differentiation of the cells and expression of UCP1.

FIG. 13 shows that exposure of CD31− cells to rosiglitazone or BMP7 robustly increases the differentiation of the cells and expression of UCP1. UCP1 mRNA expression in human fetal muscle-derived CD31− cells at day 16 of differentiation were measured.

All the cells were grown for 3 days in proliferation medium (EGM2) and then (on day 0) placed for 16 days in adipogenic differentiation medium (Minimal Differentiation Medium, MDM). The "EGM2" cells were maintained in EGM2 medium all along. Rosiglitazone (1 microM) was added from day 0 and kept in the medium until the end of the study. BMP7 (6 nM) was added 2 days before day 0 and removed at day 0. Effects of differentiation medium (MDM vs. EGM2), rosiglitazone (MDM+rosi vs. MDM) and BPM7 (MDM+BMP7 vs. MDM) are shown as fold change (as compared to EGM2 cells) on UCP1 mRNA expression in human muscle-derived brown adipocyte progenitor cells (CD31-).

The results are the mean±s.e.m. of arbitrary values normalized using the corresponding cyclophilin A values. They are expressed in fold change vs. their respective non-induced (EGM2) values considered as 1 (n=3).

By contrast, in the CD31+ and CD56+ cell populations UCP1 mRNA was undetectable in all but a few samples where it was at least 1,000-fold (10 cycles) lower in abundance than in the differentiated CD31− cells.

Example 12: Quantification of UCP1 mRNA by TaqMan Real-Time PCR

Figure 18A:
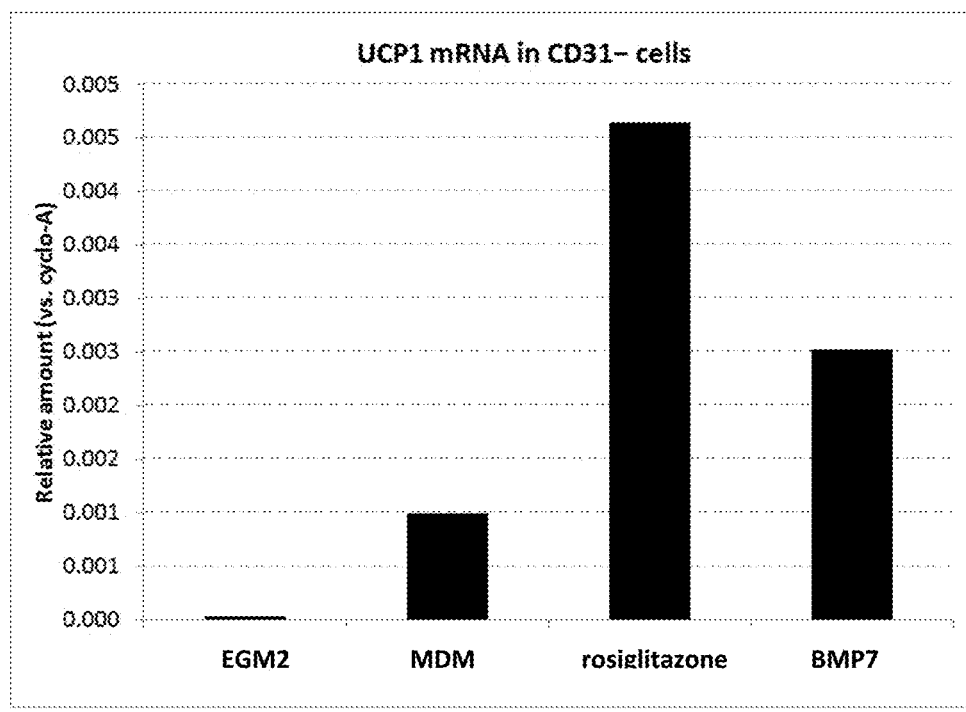
FIGS. 18A-18B show the quantification of UCP1 (FIG. 18A, black bars), FABP4 (FIG. 18B, gray bars) and cyclophilin A mRNA by multiplexed real-time PCR in undifferentiated (EGM2) and differentiated (rosiglitazone or BMP7) CD31− cells.
Figure 18B:
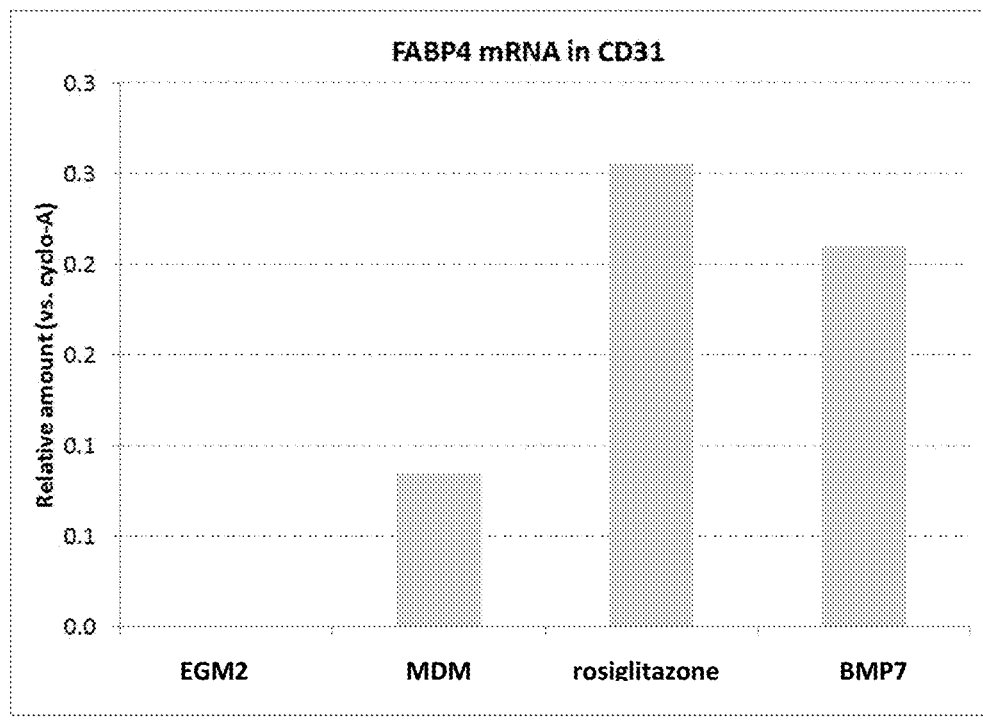

A robust method is provided herein, for detection of CD31− cell differentiation into brown adipocytes by simultaneously quantifying mRNA species corresponding to the brown adipocyte marker UCP1 (FIG. 18A), the adipocyte marker FABP4 (FIG. 18B), and the "housekeeping" gene cyclophilin A which was used as the internal control.

This method of the present invention permits analysis of a large number of samples to identify agents that enhance the differentiation of CD31- cells into brown adipocytes. When differentiated into brown adipocytes CD31− cells express much higher levels of UCP1 and FABP4 mRNA for a given level of cyclophilin A UCP1 and FABP4 mRNA levels normalized to cyclophilin A mRNA levels give an indication of the level of differentiation of the CD31− cells into brown adipocytes, independent of the total number of cells in the sample.

Quantification of UCP1, FABP4 and cyclophilin A mRNA by multiplexed TaqMan real-time PCR can thus be used to quantify differentiation of the CD31− cells into brown adipocytes.

Example 13: Quantification of UCP1 Protein by Fluorescence Immunohistochemistry (IHC)

Another robust method for detection of CD31− cell differentiation into brown adipocytes is provided herein, by quantifying UCP1 protein by fluorescence immunohistochemistry (IHC).

Using this method, UCP1 staining can be evaluated using automated high content imaging. GE Healthcare's InCell 1000 High Content Imager combines automated microscopy with high content image analysis software (InCell Developer Toolbox). The reference compound rosiglitazone was used to promote the differentiation of the CD31− cells and increase the expression of UCP1. Using a primary antibody that recognizes UCP1, Abcam ab23841, and a secondary antibody, Alexafluor 488 goat anti-rabbit antibody, we can quantify relative UCP1 levels per cell. With this method we found that rosiglitazone increased the level of UCP1 protein 7-fold (UCP1 intensity per nucleus of 105,542 with rosiglitazone vs. 14,815 without rosiglitazone) (FIG. 17A, 17B). It was also discovered that non-specific antibody background signal was very low, and the standard deviation of mean UCP1 signal per cell was very small, indicating that the assay is suitable for high content screening.

Referring to FIGS. 17A-17B, culturing and differentiation of CD31− cells into brown adipocytes were performed as described in Methods without (FIG. 17A) or with (FIG. 17B) rosiglitazone (1 μM) added to the adipogenic medium (MDM) from day 0. Cells were differentiated for 15 days, then fixed with 4% paraformaldehyde PBS pH 7.4, and incubated with a UCP1 antibody (Abcam ab23841). Alexafluor 488 goat anti-rabbit antibody was used to quantify relative UCP1 levels (green). Nuclei were stained with DAPI (blue). UCP1 signal intensity was measured using the GE Developer Toolbox software on images collected on the InCell 1000 Automated High Content Imager. Numerical data was exported in table format and screenshots of how the algorithm processed the original images were also collected.

Fluorescence IHC detection of UCP1 can thus be used with a commercially available UCP1 antibody to quantify UCP1 protein and differentiation of the CD31− cells into brown adipocytes.

Materials and Methods

Except otherwise indicated, all organic and inorganic chemicals of analytical or molecular biology grade were purchased from Sigma Chemical Co. (St Louis, Mich.) and Gibco BRL (New York, N.Y.). Rosiglitazone was purchased from Cayman Chemical (#71742) and recombinant human BMP7 (rhBMP7) was from R&D Systems (100 μg/ml, 6.3 μM, #354-BP-010).

Human Tissues

Human fetal tissues were obtained anonymously, following spontaneous, voluntary or therapeutic terminations of pregnancy, from Magee Women Hospital, University of Pittsburgh and Erasmus Medical Center, Rotterdam, The Netherlands, in compliance with the Institutional Review Board protocol. Developmental age (16 to 24 or 18 to 19 weeks of gestation) was estimated by measuring foot length.

Informed consent to the use of fetal tissues was obtained from the patients in all instances. Adult human discarded abdominal subcutaneous WAT, originating from 45-55 year old patients undergoing plastic surgery performed one year after gastric bypass, was kindly provided by Dr. Peter Rubin (Division of Plastic Surgery, University of Pittsburgh). The adult skeletal muscle tissue used for cell sorting was obtained post mortem from 50-78 year-old donors. The adult skeletal muscle used for the first group of RT-PCR studies was obtained from the rectus abdominus during surgery for either lap banding, inguinal hernia or hysterectomy of 10 lean male and female subjects. All subjects agreed to donate muscle samples during their operations and the protocol was approved by the Medical Ethical Review Committee of Deakin University. The average ages were 45±3 years and the average body mass index was 22.2±0.8. The adult skeletal muscle used for the second group of RT-PCR studies was obtained from the vastus lateralis of 7 obese type 2 diabetic male and female patients before and after 8 weeks of treatment with rosiglitazone (2×4 mg per day). The average age was 63±4 years and the average body mass index was 29.9±3.8. The complete clinical profile of the patients has been described in a previous publication [18]. All subjects agreed to donate muscle samples, and the protocol was approved by the Medical Ethical Review Committee of Maastricht University.

Adult Tissues Used for CD31− Cell Purification

Human skeletal muscle tissue samples from autopsy (25-80 year old individuals) were obtained from the National Disease Research Interchange (NDRI, Philadelphia, Pa.) and approved by NDRI's Feasibility Review Committee (protocol #BOO1).

Mice

Animals were treated in accordance with the Centre Médical Universitaire (Genève) institutional guidelines. They were housed individually and kept on a 12 h light-dark cycle in a temperature-controlled room at 24° C. They were allowed ad libitum access to water and a standard laboratory chow. The interscapular BAT of 4- to 6-week-old male 129 Sv/ev mice were excised and their precursor cells isolated and cultured as previously described [19].

Immunohistochemistry

Fresh fetal and adult tissues were gradually frozen by immersion in isopentane cooled in liquid nitrogen. 5- to 7-μm sections were cut on a cryostat (Microm HM 505 E), fixed with 50% acetone and 50% methanol, dried for 5 min at room temperature (RT), and then washed 3 times for 5 min in phosphate-buffered saline. Non-specific binding sites were blocked with 5% goat serum for 1 hour at RT. Sections were incubated overnight at 4° C. with a CD34 mouse anti-human antibody (Serotech, 1:50), then, after rinsing, for 1 hour at RT with a secondary goat anti-mouse biotinylated antibody (DAKO, 1:1000) and for 30 min at RT with streptavidin-Cy3 (Sigma, 1:1000) or for 2 hours at RT with a conjugated CD146-Alexa 488 mouse anti-human antibody (Chemicon, 1:200). Nuclei were stained with 4', 6-diamino-2-phenylindole dihydrochloride (Molecular Probes, 1:2000) for 5 min at RT. An isotype-matched negative control was performed with each immunostaining.

Quantification of UCP1 Protein by Fluorescence Immunohistochemistry (IHC)

Culturing and differentiation of CD31− cells into brown adipocytes were performed using adipogenic differentiation medium lacking (Minimal Differentiation Medium, MDM) or containing 1 μM rosiglitazone (Reference Differentiation Medium, RDM). After 15 days of differentiation cells were fixed with 4% Paraformaldehyde PBS pH 7.4, and incubated with a UCP1 antibody (Abcam ab23841) and Alexafluor 488 goat anti-rabbit antibody to quantify relative UCP1 levels (green) according to standard protocols. Prior to fixation of cells, nuclei were labeled with 5 μM DAPI (blue) for 10 minutes. Each treatment condition was evaluated in triplicate in a 96-well plate corresponding to approximately 360-480 cells for each data point in total. The InCell 1000 Developer Toolbox software was used to develop an automated cell detection script to measure UCP1 signal intensity, using the nuclei and cytoplasm detection algorithms. As a readout, total intensity of UCP1 signal within the cell was used, normalized to cell number.

Flow Cytometry

The vascular cells of fetal skeletal muscle, pancreas, lung and liver as well as of adult muscle and WAT were analysed by flow cytometry. Fresh fetal or adult muscle as well as fetal pancreas, lung and liver tissues were cut into small pieces with a scalpel in Dulbecco's Modified Eagle Medium high glucose (DMEM) containing 20% fetal bovine serum (FBS), 1% penicillin-streptomycin (PS) and collagenases IA-S, II-S and IV-S(Sigma, 1 mg/mL), then incubated at 37° C. for 75 min (fetal tissues) or 90 min (adult tissues) with constant stirring. Final cell dissociation was achieved between ground glass slides. Cells were washed with phosphate-buffered saline and centrifuged for 5 min at 350 g. They were resuspended in DMEM, 20% FBS, filtered at 100 μm, stained with Trypan blue and counted after dead cell exclusion. The WAT stroma vascular fraction was prepared by collagenase digestion according to Champigny et al. [20].

Cells ($10^5$ for analysis and around $30 \times 10^6$ for sorting) were incubated with one of the following directly coupled mouse anti-human antibodies: CD45-APC Cy7 (Santa Cruz Biotechnologies, 1:200), CD45 PerCP Cy5.5 (eBioscience #45-0459-73, 1:10), CD56-PE Cy7 (BD Pharmigen 1:100), CD56 APC (BD Pharmigen #555518, 1:50), CD34-PE (DAKO, 1:100 or BD Pharmigen #555822, 1:20), CD146 unconjugated, BD Pharmigen: PE mouse anti-human CD146 (BD Pharmigen #550315, 1:50), CD146-FITC (Serotec, 1:100), and anti-human CD31 (PECAM-1) FITC (eBioscience #11-0319-42, 1:10), each in 1 ml DMEM, 20% FBS, 1% penicillin-streptomycin (PS), at 4° C. for 15 min. After washing and centrifugation, cells were incubated with 7-amino-actinomycin D (7-AAD, BD Pharmigen, 1:100) or the dye Hoechst 33528 at 1 μg/ml (Molecular Probes-Invitrogen #H3569) for cell viability/dead cell exclusion, filtered at 70 μm and run on a FACS Aria flow cytometer (Becton Dickinson). As negative controls, cell aliquots were incubated with isotype-matched mouse IgGs conjugated to APC Cy7 (BD Pharmigen, 1:100), PE Cy7 (BD Pharmigen, 1:100), PE (Chemicon, 1:100) and FITC (US Biological, 1:100) under the same conditions.

Cell Culture

Cells were seeded at 10,000 per $cm^2$ in 0.2% gelatin coated plates (24-well, BD Falcon #353047), cultured until confluency (2-4 days) at 37° C. in Endothelial cell growth medium-2 (EGM2) (BulletKit growth medium, Lonza #CC-3162) and until differentiation (10-16 more days). After 2 or 3 days in EGM2 medium the cells were induced to differentiate by replacing the medium with an adipogenic medium, which is a modification of the adipogenic medium described by Rodriguez et al. [21] and may or may not contain a differentiation inducing agent (e.g., PPARγ agonist). The MDM described above contains: DMEM/Ham's F-12 50/50 Mix (3.151 g/l, 17.5 mM D-glucose, 3.651 g/l L-glutamine) (Cellgro #10-090-CV), 5 μg/ml (0.86 μM) insulin, 10 μg/ml transferrin, 0.2 nM 3,3',5-triiodo-L-thyronine, 100 μM 3-isobutyl-1-methylxanthine, 1 μM dexamethasone, and 1% penicillin-streptomycin. If rosiglitazone is used as a differentiation inducing agent, it can be supplied at 1 µM or any other concentration sufficient to induce differentiation of BAT progenitor cells into adipocytes.

For cell expansion studies, confluent cells grown in EGM2 medium only were detached by treatment with trypsin-EDTA for 3-5 min at 37° C., and then split 1:3 or 1:4 and cultured as described above. Human white adipocytes in primary culture used in the oximetry studies were obtained as previously described [22].

RT-PCR

Total cell RNA was prepared using the kit NucleoSpin® RNAII (Clontech, Palo Alto, Calif.), Extract-all solution (Eurobio, Courtaboeuf, France) or PureLink RNA Isolation Kit (Invitrogen #12183-016) and quantified by Biophotometry (Biophotometer, Eppendorf). Oligo-dT primed First strand cDNA were synthesized using the Superscript™ II RNase H Reverse Transcription kit (Invitrogen, Carlsbad, Calif.) and oligo-dT primers or the High Capacity cDNA Reverse Transcription kit (Applied Biosystems, Foster City, Calif.) and random primers.

Quantitative real-time PCR was performed using ABI rapid thermal cycler system and a SYBR Green PCR master mix (Applied Biosystems, Foster City, Calif.), or an ABI 7300 Real-time PCR instrument, a TaqMan Gene Expression Master Mix (Applied Biosystems #4369016) and TaqMan Gene Expression Pre-formulated Assays for human uncoupling protein-1 (GenBank NM_021833) (Applied Biosystems Assay ID Hs01084772_m1, TaqMan Gene Expression Assay part #4351372) and for human peptidyl-prolyl isomerase A "cyclophilin A" (GenBank NM_021130) (Applied Biosystems Assay ID Hs99999904_m1, TaqMan® Gene Expression Assay part #4448485). Cyclophilin A was used as a control to account for any variations due to the efficiency of the reverse transcription. The upstream and downstream oligonucleotide primers were chosen on both sides of an intron to prevent amplification of contaminating genomic DNA.

The primers used for real time quantitative PCR in human cells and in mouse brown adipocytes are as follows:
hUCP1

```
Sense primer:
                                        (SEQ ID NO: 1)
5'-CCTCACCGCAGGGAAAGAA-3'

Antisense primer:
                                        (SEQ ID NO: 2)
5'-CTAACGACTGGAGGAGTGGCA-3'
```

Amplicon position: 429-504
Accession No.: NM_021833
mUCP1

```
Sense primer:
                                        (SEQ ID NO: 3)
5'-CGATGTCCATGTACACCAAGGA-3'

Antisense primer:
                                        (SEQ ID NO: 4)
5'-TTGTGGCTTCTnTCTGCGA-3'
```

Amplicon position: 996-1063
Accession No.: NM_009463.2 hleptin

```
Sense primer:
                                        (SEQ ID NO: 5)
5'-CCAAAACCCTCATCAAGACAATT-3'

Antisense primer:
                                        (SEQ ID NO: 6)
5'-AAGTCACCGGTTTGGACTTCA-3'
```

Amplicon position: 143-238
Accession No.: BC069323
heyclophilin A

```
Sense primer:
                                        (SEQ ID NO: 7)
5'-CATCTGCACTGCCAAGACTGA-3'

Antisense primer:
                                        (SEQ ID NO: 8)
5'-GCAAAGTGAAAGAAGGCATGAA-3'
```

Amplicon position: 466-537
Accession No.: NM_203431
mcyclophilin A

```
Sense primer:
                                        (SEQ ID NO: 9)
5'-CAAATGCTGGACCAAACACAA-3'

Antisense primer:
                                        (SEQ ID NO: 10)
5'-CCATCCAGCCATTCAGTCTTG-3'
```

Amplicon position: 343-412
Accession No.: NM_008907
Primers used for real time quantitative PCR in human skeletal muscle are as follows:
hUCP1

```
Sense primer:
                                        (SEQ ID NO: 11)
5'-TCCGGCTCCAGGTCCAA-3'

Antisense primer:
                                        (SEQ ID NO: 12)
5'-TGATTGTTCCCAGGACACCTTT-3'
```

Amplicon position: 240-311
Accession No.: NM_021833
hcyclophilin A

```
Sense primer:
                                        (SEQ ID NO: 7)
5'-CATCTGCACTGCCAAGACTGA-3'

Antisense primer:
                                        (SEQ ID NO: 8)
5'-GCAAAGTGAAAGAAGGCATGAA-3'
```

Amplicon position: 466-537
Accession No.: NM_203431
Sequences and primers used for analytical PCR are as follows:
CD31
Accession No.: NM_000442
CD34

```
Sense primer:
                                        (SEQ ID NO: 13)
5'-CATCACTGGCTATTTCCTGATG-3'
```

-continued

Antisense primer:
(SEQ ID NO: 14)
5'-AGCCGAATGTGTAAAGGACAG-3'

Amplicon position: 1172-1591
Accession No.: M81104
CD56

Sense primer:
(SEQ ID NO: 15)
5'-GTATTTGCCTATCCCAGTGCC-3'

Antisense primer:
(SEQ ID NO: 16)
5'-CATACTTCTTCACCCACTGCTC-3'

Amplicon position: 542-873
Accession No.: BC014205
CD45

Sense primer:
(SEQ ID NO: 17)
5'-CATGTACTGCTCCTGATAAGAC-3'

Antisense primer:
(SEQ ID NO: 18)
5'-GCCTACACTTGACATGCATAC-3'

Amplicon position: 940-1579
Accession No.: Y00638
CD146

Sense primer:
(SEQ ID NO: 19)
5'-AAGGCAACCTCAGCCATGTCG-3'

Antisense primer:
(SEQ ID NO: 20)
5'-CTCGACTCCACAGTCTGGGAC-3'

Amplicon position: 168-603
Accession No.: M28882
β-actin

Sense primer:
(SEQ ID NO: 21)
5'-CCTCGCCTTTGCCGATCC-3'

Antisense primer:
(SEQ ID NO: 22)
5'-GGAATCCTTCTGACCCATGC-3'

Amplicon position: 25-229
Accession No.: NM_001101.

Arbitrary units were determined by normalizing target mRNA levels to cyclophilin mRNA levels (based on Cts), wherein the cyclophilin levels were first divided by 100,000 for ease of reference. For example, a ratio of target mRNA to cyclophilin mRNA of 0.01797 is expressed as 1797.

Alternatively, quantitative real-time PCR was performed using an Applied Biosystems 7300 real-time PCR instrument (with SDS Software v1.4.0.25), TaqMan Gene Expression Master Mix (Applied Biosystems #4369016), and TaqMan Gene Expression Pre-formulated Assays for human uncoupling protein-1 "UCP1" (GenBank NM_021833) [FAM MGB probe] (Applied Biosystems Assay ID Hs00222453_m1, TaqMan Gene Expression Assay part #4351370) and for human peptidylprolyl isomerase A "cyclophilin A" (GenBank NM_021130) [VIC MGB probe] (Applied Biosystems Assay ID Hs99999904_m1, TaqMan Gene Expression Assay part #4448485). Custom TaqMan Gene Expression reagents were developed for simultaneous measurement of human fatty acid binding protein 4 "FABP4" (GenBank NM_001442) in a multiplexed fashion (with UCP1 and cyclophilin A): TaqMan MGB Probe [NED]: CAG GAA AGT CAA GAG CAC CA (Applied Biosystems #4316034; SEQ ID NO:30), Sense primer: TCA TAC TGG GCC AGG AAT TT (Applied Biosystems #4304971; SEQ ID NO:31) and Antisense primer: TGC ACA TGT ACC AGG ACA CC (Applied Biosystems #4304971; SEQ ID NO:32).

Cyclophilin A was used as a control to account for any variations due to the efficiency of reverse transcription. Arbitrary units were determined by normalizing target mRNA levels to cyclophilin A mRNA levels (based on Cts).

Validation of the Human UCP1 Amplicon

The PCR-amplified fragment was cloned into the pCR2.1-TOPO vector through the TOPO-TA cloning system (Invitrogen, Carlsbad, Calif.) and purification of color-selected colonies was performed using the Qiaprep Spin Miniprep (Qiagen, Hilden, Germany). Sequences were determined with oligonucleotide M 13 Reverse on the pCR2.1-TOPO vector using the Applied Biosystem Big Dye sequencing kit on an ABI 3700 automated sequencer (Applied Biosystems, Foster City, Calif.).

Western Blots

Cultured cells were collected with a rubber policeman in 200 µl of RIPA buffer (150 mM NaCl, 1% Nonidet P-40, 0.5% Na deoxycholate, 0.1% SDS, 1:200 protease inhibitor cocktail (Sigma Chemical Co, St Louis, Mich.) and 50 mM Tris/HCl pH 8.0). Human BAT and skeletal muscle were homogenized in the above RIPA buffer. The protein content was determined according to the technique of Lowry [23]. Western blots were performed as previously described [24]. The UCP1 protein was detected using a 1/500 diluted rabbit anti-mouse UCP1 polyclonal primary antibody generously provided by Dr. B. Cannon (Stockholm, Sweden). This antibody had been raised against the C-terminal decapeptide of mouse UCP1, that shares 80% identity with human UCP1 and 0 and 10% identities with human UCP2 and UCP3, respectively. Glyceraldehyde phosphate dehydrogenase (GAPDH) protein was detected using a 1/5000 diluted mouse anti-mouse GAPDH monoclonal primary antibody (Chemicon International, Inc, Temecula, Calif.). 1/5000 diluted goat anti-rabbit or anti-mouse peroxidase-labelled secondary antibodies (Sigma-Aldrich, St. Louis, Mo. or Bio-Rad, Hercules, Calif.) were used. A SeeBlue® Plus 2 Pre-stained Standard Ladder (Invitrogen, Carlsbad, Calif.) was used. Protein signals were detected by chemiluminescence using a standard ECL kit and developed on a Hyperfilm ECL film.

High-Resolution $O_2$ Consumption Measurement

Oxygen consumption was measured using a 2-injection chambers respirometer equipped with a Peltier thermostat, Clark-type electrodes, and integrated electromagnetic stirrers (Oroboros® Oxygraph, Oroboros, Innsbruck, Austria). Measurements were performed at 37° C. with continuous stirring in 2 ml of DMEM F12, 10% new born calf serum. Under these conditions, the serum provided the fatty acids necessary to sustain UCP1 uncoupling activity. Before each 02 consumption measurement, the medium in the chambers was equilibrated with air for 30 min, and freshly trypsinized cells were transferred into the respirometer glass chambers. After observing steady-state respiratory flux, ATP synthase was inhibited with oligomycin (0.25-0.5 mg/l) and cells were titrated with the uncoupler carbonyl cyanide 3-chlorophenylhydrazone up to optimum concentrations in the range of 1-2 μM. The respiratory chain was inhibited by antimycin A (1 μg/ml). Oxygen consumption was calculated using DataGraph software (Oroboros software).

CD31− Cell Respiration Measurement

Respiration rate of CD31− cells before differentiation and upon differentiation into brown adipocytes was measured using a Seahorse Bioscience XF24 Extracellular Flux Analyzer (Seahorse Bioscience, Billerica, Mass.). Adult-derived CD31− cells were first cultured in Seahorse plates in either EGM2 (i.e., undifferentiated progenitors) or MDM and rosiglitazone (1 μM)+BMP7 (6 nM) for 3 days (fully differentiated brown adipocytes). Next, measurements of respiration were taken at baseline, in the presence of oligomycin (5 μM) (so-called "State 4" respiration, or proton leak) and in the presence of FCCP (titration: 0.5 μM, 1 μM and 5 μM) (so-called "State 3u" respiration, or maximally uncoupled).

Gene Chip Analysis

The total RNA of fetal muscle CD34+ cells expanded in culture for up to 3 passages (4 weeks) and of human muscle biopsies were prepared as described above. The quality assurance measurements, the preparation of the cRNA targets and the gene chip analyses using Illumina Human WG-6 BeadChip were performed by Expression Analysis, Inc. (Durham, N.C.). BeadStudio nonparametric methods were used for the computation of Detection P-Values.

Statistical Analysis

Data are expressed as means±s.e.m. Significances were evaluated using the unpaired Student's t-test. A paired Student's t-test was used to determine the effects of rosiglitazone on human skeletal muscle UCP1 mRNA levels. Significances were set at $p<0.05$.

Cloning of the Human UCP1 Promoter/Enhancer Region

To develop a screening strategy, the human UCP1 promoter/enhancer was subcloned as follows.

A human BAC (bacterial artificial chromosome) clone #RP11-5K16 (AC 108019) containing the human UCP1 (uncoupling protein-1) promoter/enhancer region was obtained from the CHORI (Children's Hospital Oakland Research Institute) BAC-PAC resources service. The selected promoter/enhancer region starts at position −25 upstream of the 5' UTR (UnTranslated Region) of the human UCP1 gene (accession number: NM_021833). Based on the human UCP1 gene initiation codon, the full cloned promoter/enhancer sequence locates between position −149 and −6269.

Primer sets were designed to amplify either:

(i) the full targeted promoter/enhancer region (6120 bp starting at position −25 upstream of the UCP1 5' UTR):

```
Left primer:
                                    (SEQ ID NO: 23)
5'-TCGTAAGCTTAGAGGCGGCGGCTGCAGACGGAGCGCGGTGTT-3'

Right primer:
                                    (SEQ ID NO: 24)
5'- ACGAAGATCTCATTACCCCAAATAGCATCACA-3'
```

(ii) the proximal targeted promoter/enhancer region (3685 bp upstream of the −25 nucleotide of the UCP1 5' UTR):

```
Left primer:
                                    (SEQ ID NO: 25)
5'-TCGTAAGCTTAGAGGCGGCGGCTGCAGACGGAGCGCGGTGTT-3'

Right primer:
                                    (SEQ ID NO: 26)
5'- ACGAACCGGTCAGAAGTGGTGAAGCCAGCCTGC-3'
```

(iii) the distal targeted promoter/enhancer region (2435 bp upstream of the proximal targeted promoter/enhancer region) as indicated:

```
Left primer:
                                    (SEQ ID NO: 27)
5'- TCGTACCGGTACAGGCTCTGGGAAGTAGGAGAAAGT-3'

Right primer:
                                    (SEQ ID NO: 28)
5'- ACGAAGATCTCATTACCCCAAATAGCATCACA-3'
```

Each primer contains a restriction site to facilitate subsequent cloning in mammalian expression vector (see below).

Cloning of the promoter/enhancer in PCR reaction was performed with 500 ng of BAC #RP11-5K16 as template, using Takara Ex Taq DNA Polymerase kit (Clontech) for amplification. PCR program steps were as follow: Initialization step: 92° C. for 2 minutes; followed by 28 cycles of: [denaturation: 92° C., 30 seconds; annealing: 59° C., 40 seconds; extension: 68° C., 5 minutes 30 second]; with a final elongation step: 68° C., 8 minutes.

The full promoter/enhancer, proximal or distal promoter/enhancer were subsequently subcloned in the reporter/MAR element-containing vector pl_68_GFP at the BglII/HindIII sites, replacing the SV40 promoter cassette [25]. Alternatively, the luciferase-based pGL3 Basic vector (Promega) was also used as another reporter type, using the same BglII/NcoI sites for subcloning purpose.

The human UCP1 promoter sequence cloned was confirmed by state-of-the-art sequencing, performed at biotechnology company, Fastens SA, Switzerland. The sequence of the human UCP1 promoter sequence is provided in the Sequence Listing as SEQ ID NO:29, wherein the entire Sequence Listing is incorporated by reference in its entirety.

Pictures for Cell Morphology

Pictures of cells were taken using a hand-held digital camera (Nikon Coolpix 950) and inverted microscope (Nikon TMS) used for cell culture observations; images were optimized using Adobe Photoshop Elements 8 functions for Auto Contrast and Auto Levels.

The section headings and subheadings used in this specification are for organizational purposes only and are not to be construed as limiting the subject matter described in any way. Further, while the present teachings are described in conjunction with various embodiments, it is not intended that the present teachings be limited to such embodiments. On the contrary, the present teachings encompass various alternatives, modifications, and equivalents as will be appreciated by those of skill in the art.

Other Embodiments

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention provides among other things novel methods and compositions for BAT progenitor cells. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

The Sequence Listing filed as an ASCII text file via EFS-Web (file name: "130204_010202_SEQListing"; date of creation: Mar. 27, 2015; size: 14,155 bytes) is hereby incorporated by reference in its entirety.

REFERENCES

[1] M. Klingenspor, Cold-induced recruitment of brown adipose tissue thermogenesis, Exp Physiol. 88 (2003) 141-148.
[2] B. Cannon, J. Nedergaard, The biochemistry of an inefficient tissue: brown adipose tissue, Essays Biochem. 20 (1985) 110-164.
[3] N. J. Rothwell, M. J. Stock, A role for brown adipose tissue in diet-induced thermogenesis, Nature. 281 (1979) 31-35.
[4] B. B. Lowell, V. S-Susulic, A. Hamann, J A Lawitts, J. Himms-Hagen, B. B. Boyer, L. P. Kozak, J. S. Flier, Development of obesity in transgenic mice after genetic ablation of brown adipose tissue, Nature 366 (1993) 740-742.
[5] H. M. Feldmann, V Golozoubova, B. C. M. Cannon, J. Nedergaard, UCP1 ablation induces obesity and abolishes diet-induced thermogenesis in mice exempt from thermal stress by living at thermoneutrality, Cell Metab. 9 (2009) 203-209.
[6] J. Kopecky, G. Clarke, S. Enerback, B. Spiegelman, L. P. Kozak, Expression of the mitochondrial uncoupling protein gene from the aP2 gene promoter prevents genetic obesity, J Clin Invest. 96 (1995).
[7] K. Tsukiyama-Kohara, F. Poulin, M. Kohara, C T. DeMaria, A. Cheng, Z. Wu, A. C. Gingras, A. Katsume, M. Elchebly, B. M. Spiegelman, M. E. Harper, M. L. Tremblay, N. Sonenberg, Adipose tissue reduction in mice lacking the translational inhibitor 4E-BP1, Nature Medicine 7 (2001) 1128-1132.
[8] K. Almind, M. Manieri, W. I. Sivitz, S. Cinti, C R. Kahn, Ectopic brown adipose tissue in muscle provides a mechanism for differences in risk of metabolic syndrome in mice, Proc Natl Acad Sci USA. (2007).
[9] M. Del Mar Gonzalez-Barroso, D. Ricquier, A. M. Cassard-Doulcier, The human uncoupling protein-1 gene (UCP1): present status and perspectives in obesity research, Obes Rev. 1 (2000) 61-72.
[10] B. Cannon, J. Nedergaard, Brown adipose tissue: function and physiological significance, Physiol Rev. 84 (2004) 277-359.
[11] W. D. van Marken Lichtenbelt, J. W. Vanhommerig, N. M. Smulders, J. M. Drossaerts, G. J. Kemerink, N. D. Bouvy, P. Schrauwen, G. J. Teule, Cold-activated brown adipose tissue in healthy men, N Engl J Med. 360 (2009) 1500-1508.
[12] A. M. Cypess, S. Lehman, G. Williams, I. TaI, D. Rodman, A. B. Goldfine, F. C Kuo, E. L. Palmer, Y. H. Tseng, A. Doria, G. M. Kolodny, C R. Kahn, Identification and importance of brown adipose tissue in adult humans, N Engl J Med. 360 (2009) 1509-1517.
[13] K. A. Virtanen, M. E. Lidell, J. Orava, M. Heglind, R. Westergren, T. Niemi, M. Taittonen, J. Laine, N. J. Savisto, S. Enerback, P. Nuutila, Functional brown adipose tissue in healthy adults, N Engl J Med. 360 (2009) 1518-1525.
[14] H. L. Garstka, W. E. Schmitt, J. Schultz, B. Sogl, B. Silakowski, A. Perez-Martos, J. Montoya, R. J. Wiesner, Import of mitochondrial transcription factor A (TFAM) into rat liver mitochondria stimulates transcription of mitochondrial DNA, Nucleic Acids Res. 31 (2003) 5039-5047.
[15] Z. Wu, P. Puigserver, B. M. Spiegelman, Transcriptional activation of adipogenesis, Curr Opin Cell Biol. 11 (1999) 689-694.
[16] Z. Zhou, T. S. Yon, Z. Chen, K. Guo, C P. Ng, S. Ponniah, S. C. Lin, W. Hong, P. Li, Cidea-deficient mice have lean phenotype and are resistant to obesity, Nat Genet. 35 (2003) 49-56.
[17] L. A. Foellmi-Adams, B. M. Wyse, D. Herron, J. Nedergaard, R. F. Kletzien, Induction of uncoupling protein in brown adipose tissue. Synergy between norepinephrine and pioglitazone, an insulin-sensitizing agent, Biochem Pharmacol. 52 (1996) 693-701.
[18] M. Mensink, M. K. Hesselink, A. P. Russell, G. Schaart, J. P. Sets, P. Schrauwen, Improved skeletal muscle oxidative enzyme activity and restoration of PGC-I alpha and PPAR beta/delta gene expression upon rosiglitazone treatment in obese patients with type 2 diabetes mellitus, Int J Obes (Lond). 31 (2007) 1302-1310.
[19] L. Lehr, K. Canola, C. Asensio, M. Jimenez, F. Kuehne, J. P. Giacobino, P. Muzzin, The control of UCP1 is dissociated from that of PGC-I alpha or of mitochondriogenesis as revealed by a study using beta-less mouse brown adipocytes in culture, FEBS Lett. 580 (2006) 4661-4666.
[20] O. Champigny, B. R. Holloway, D. Ricquier, Regulation of UCP gene expression in brown adipocytes differentiated in primary culture. Effects of a new beta-adrenoceptor agonist, Mol Cell Endocrinol. 86 (1992) 73-82.
[21] A. M. Rodriguez, C. Elabd, F. Delteil, J. Astier, C. Vernochet, P. Saint-Marc, J. Guesnet, A. Guezennec, E. Z. Amri, C. Dani, G. Ailhaud, Adipocyte differentiation of multipotent cells established from human adipose tissue, Biochem Biophys Res Commun 315 (2004) 255-263.
[22] J. Corre, V. Planat-Benard, J. X. Corberand, L. Penicaud, L. Casteilla, P. Laharrague, Human bone marrow adipocytes support complete myeloid and lymphoid differentiation from human CD34 cells, Br J Haematol. 227 (2004) 344-347.

[23] O. H. Lowry, N. J. Rosebrough, A. L. Farr, R. J. Randall, Protein measurement with the Folin phenol reagent, J Biol Chem. 193 (1951) 265-275.

[24] M. Jimenez, C. Yvon, L. Lehr, B. Leger, P. Keller, A. Russell, F. Kuhne, P. Flandin, J. P. Giacobino, P. Muzzin, Expression of uncoupling protein-3 in subsarcolemmal and intermyofibrillar mitochondria of various mouse muscle types and its modulation by fasting, Eur J Biochem. 269 (2002) 2878-2884.

[25] P. A. Girod, D. Q. Nguyen, D. Calabrese, S. Puttini, M. Grandjean, D. Martinet, A. Regamey, D. Saugy, J. S. Beckmann, P. Bucher, N. Mermod, Genome-wide prediction of matrix attachment regions that increase gene expression in mammalian cells, Nat Methods. 4 (2007) 747-773.

[26] Tseng Y H, Kokkotou E, Schulz T J, Huang T L, Winnay J N, Taniguchi C M, Tran T T, Suzuki R, Espinoza D O, Yamamoto Y, Ahrens M J, Dudley A T, Norris A W, Kulkarni R N, Kahn C R. New role of bone morphogenetic protein 7 in brown adipogenesis and energy expenditure. Nature. 2008 Aug. 21; 454(7207):1000-4. PubMed PMID: 18719589; PubMed Central PMCID: PMC2745972.

[27] Zhang H, Schulz T J, Espinoza D O, Huang T L, Emanuelli B, Kristiansen K, Tseng Y H. Cross talk between insulin and bone morphogenetic protein signaling systems in brown adipogenesis. Mol Cell Biol. 2010 September; 30(17):4224-33. Epub 2010 Jun. 28. PubMed PMID: 20584981; PubMed Central PMCID: PMC2937545.

[28] Schulz T J, Huang T L, Tran T T, Zhang H, Townsend K L, Shadrach J L, Cerletti M, McDougall L E, Giorgadze N, Tchkonia T, Schrier D, Falb D, Kirkland J L, Wagers A J, Tseng Y H. Identification of inducible brown adipocyte progenitors residing in skeletal muscle and white fat. Proc Natl Acad Sci USA. 2011 Jan. 4; 108(1):143-8. Epub 2010 Dec. 20. PubMed PMID: 21173238; PubMed Central PMCID: PMC3017184.

The invention claimed is:

1. A method for identifying an agent that induces differentiation of a brown adipocyte progenitor cell into a brown adipocyte, comprising:
   contacting a population of skeletal muscle cells with a first and a second antibody that are specific for CD34 and CD31, respectively;
   selecting a brown adipocyte progenitor cell from the population of skeletal muscle cells on the basis of expression of CD34 and CD31, wherein said brown adipocyte progenitor cell is positive for CD34 and negative for CD31;
   contacting the selected brown adipocyte progenitor cell with an agent that induces differentiation brown adipocyte progenitor cell into a brown adipocyte; and
   determining in the brown adipocyte progenitor cell the presence of an indicator of differentiation into a brown adipocyte induced by said agent.

2. The method of claim 1, wherein the indicator of differentiation is an increase in one or more of the following: expression of uncoupling protein-1 (UCP1) protein or mRNA, expression of fatty acid-binding protein-4 (FABP4) (aP2) protein or mRNA, expression of peroxisome-proliferator-activated receptor γ2 (PPARγ2) protein or mRNA, expression of mitochondrial transcription factor A (mtTFA) protein or mRNA, expression of PPARγ coactivator-1α (PGC-1α) protein or mRNA, uncoupled respiration, respiration rate, metabolic rate, glucose utilization rate, fatty acid oxidation rate, and a combination thereof.

3. The method of claim 1, wherein the population of skeletal muscle cells is further contacted with an antibody specific for CD146 and the selected brown adipocyte progenitor cell is negative for CD146.

4. The method of claim 1, wherein the population of skeletal muscle cells is further contacted with an antibody specific for CD45 and the selected brown adipocyte progenitor cell is negative for CD45.

5. The method of claim 1, wherein the population of skeletal muscle cells is further contacted with an antibody specific for CD56 and the selected brown adipocyte progenitor cell is negative for CD56.

6. The method of claim 1, wherein the agent is one or more of the following: a peroxisome-proliferator-activated receptor (PPAR)γ activator, modulator or inhibitor; a PPARγ activator or modulator; a PPARγ activator or modulator; a dual PPARγ and PPARγ activator or modulator; a pan-PPAR (α, δ, γ) activator or modulator; a phosphodiesterase (PDE)4 inhibitor; a PDE7 inhibitor; a nuclear receptor-interacting protein 1 (NRIP1) (RIP 140) inhibitor, a phosphatase and tensin homolog (PTEN) inhibitor; an α1-adrenergic full or partial agonist; a retinoid receptor α (RXRα) activator or modulator; a PPARγ coactivator (PGC)-1α activator; a PGC-1β inhibitor or activator; adiponectin or an activator of adiponectin receptor AdipoR1 and/or AdipoR2; a nitric oxide synthase (NOS) inhibitor or activator; a Rho kinase-ROCK inhibitor; brain-derived neurotrophic factor (BDNF); a monoamine oxidase (MAO) A inhibitor and/or an MAO B inhibitor; an activator of SRC proto-oncoprotein; an inhibitor of epidermal growth factor receptor (EGFR); an inhibitor of fatty acid amide hydrolase (FAAH); an inhibitor of mitogen-activated protein kinase (MAPK) 1 or 2 or 4 or 5 or 7 or 8; an inhibitor of cyclin-dependent kinase 9 (CDK9); a TGR5 agonist; an adenosine monophosphate activated protein kinase (AMPK) activator; bone morphogenetic protein 7 (BMP-7); an mammalian target of rapamycin (mTOR) inhibitor; an adenylate cyclase activator; or combinations of any of the foregoing.

7. The method of claim 1, wherein the indicator of differentiation is an increase in one or both of uncoupling protein-1 (UCP1) protein and UCP1 mRNA.

8. The method of claim 1, wherein the brown adipocyte progenitor cell is capable of expansion and passage in a culture.

9. The method of claim 1, wherein the population of skeletal muscle cells is obtained from one or more of fetal, juvenile, and adult human skeletal muscle.

10. A method for identifying an agent that induces differentiation of a brown adipocyte progenitor cell into a brown adipocyte, comprising:
    contacting a population of skeletal muscle cells with a first and a second antibody that are specific for CD34 and CD31, respectively;
    selecting a plurality of brown adipocyte progenitor cells from the population of skeletal muscle cells on the basis of expression of CD34 and CD31, wherein said brown adipocyte progenitor cell is positive for CD34 and negative for CD31;
    contacting the selected brown adipocyte progenitor cell with an agent that induces differentiation brown adipocyte progenitor cell into a brown adipocyte; and
    determining in the plurality of brown adipocyte progenitor cells the presence of an indicator of differentiation into a brown adipocyte induced by said agent.

11. The method of claim 10, wherein the indicator of differentiation is an increase in one or both of uncoupling protein-1 (UCP1) protein and UCP1 mRNA in the plurality of brown adipocyte progenitor cells.

12. The method of claim 10, wherein the agent is one or more of the following: a PPARγ activator, modulator or inhibitor; a PPARα activator or modulator; a PPARδ activator or modulator; a dual PPARα and PPARδ activator or modulator; a pan-PPAR (α, δ, γ) activator or modulator; a PDE4 inhibitor; a PDE7 inhibitor; a NRIP1 (RIP 140) inhibitor, a PTEN inhibitor; an α1-adrenergic full or partial agonist; an RXRα activator or modulator; a PGC-1α activator; a PGC-1β inhibitor or activator; adiponectin or an activator of adiponectin receptor AdipoR1 and/or AdipoR2; an NOS inhibitor or activator; a Rho kinase-ROCK inhibitor; BDNF; a monoamine oxidase (MAO) A inhibitor and/or an MAO B inhibitor; an activator of SRC proto-oncoprotein; an inhibitor of EGFR; an inhibitor of FAAH; an inhibitor of MAPK 1 or 2 or 4 or 5 or 7 or 8; an inhibitor of CDK9; a TGR5 agonist; an AMPK activator; BMP-7; an mTOR inhibitor; an adenylate cyclase activator; or combinations of any of the foregoing.

13. The method of claim 10, wherein the brown adipocyte progenitor cell is capable of expansion and passage in a culture.

14. The method of claim 10, wherein the population of skeletal muscle cells is obtained from one or more of fetal, juvenile, and adult human skeletal muscle.

15. The method of claim 10, wherein the population of skeletal muscle cells is further contacted with an antibody specific for CD146 and the selected brown adipocyte progenitor cells are negative for CD146.

16. The method of claim 10, wherein the population of skeletal muscle cells is further contacted with an antibody specific for CD45 and the selected brown adipocyte progenitor cells are negative for CD45.

17. The method of claim 10, wherein the population of skeletal muscle cells is further contacted with an antibody specific for CD56 and the selected brown adipocyte progenitor cells are negative for CD56.

* * * * *

SEQUENCE LISTING

```
<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: Synthetic DNA

<400> SEQUENCE: 1
cctcaccgca gggaaagaa                                                  19

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
ctaacgactg gaggagtggc a                                               21

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
cgatgtccat gtacaccaag ga                                              22

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
ttgtggcttc ttttctgcga                                                 20

<210> SEQ ID NO 5
```

```
<211> LENGTH: 23
<212> TYPE: DNA
<213> ORGANISM: Artificial Sequence
<220> FEATURE:
<223> OTHER INFORMATION: Synthetic DNA

<400> SEQUENCE: 5
ccaaaaccct catcaagaca att                                           23

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
aagtcaccgg tttggacttc a                                             21

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
catctgcact gccaagactg a                                             21

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8
gcaaagtgaa agaaggcatg aa                                            22

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
caaatgctgg accaaacaca a                                             21

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
ccatccagcc attcagtctt g                                             21

<210> SEQ ID NO 11
<211> LENGTH: 17
<212> TYPE: DNA
<213> ORGANISM: Artificial Sequence
<220> FEATURE:
<223> OTHER INFORMATION: Synthetic DNA

<400> SEQUENCE: 11
```

```
tccggctcca ggtccaa                                            17
```

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12

```
tgattgttcc caggacacct t                                       21
```

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13

```
catcactggc tatttcctga tg                                      22
```

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14

```
agccgaatgt gtaaaggaca g                                       21
```

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15

```
gtatttgcct atcccagtgc c                                       21
```

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA

<400> SEQUENCE: 16

```
catacttctt cacccactgc tc                                      22
```

<210> SEQ ID NO 17
<211> LENGTH: 22
<212> TYPE: DNA
<213> ORGANISM: Artificial Sequence
<220> FEATURE:
<223> OTHER INFORMATION: Synthetic DNA

<400> SEQUENCE: 17

```
catgtactgc tcctgataag ac                                      22
```

<210> SEQ ID NO 18
<211> LENGTH: 21
<212> TYPE: DNA

```
<213> ORGANISM: Artificial Sequence
<220> FEATURE:
<223> OTHER INFORMATION: Synthetic DNA

<400> SEQUENCE: 18
gcctacactt gacatgcata c                                             21

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA

<400> SEQUENCE: 19
aaggcaacct cagccatgtc g                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
ctcgactcca cagtctggga c                                             21

<210> SEQ ID NO 21
<211> LENGTH: 18
<212> TYPE: DNA
<213> ORGANISM: Artificial Sequence
<220> FEATURE:
<223> OTHER INFORMATION: Synthetic DNA

<400> SEQUENCE: 21
cctcgccttt gccgatcc                                                 18

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
ggaatccttc tgacccatgc                                               20

<210> SEQ ID NO 23
<211> LENGTH: 42
<212> TYPE: DNA
<213> ORGANISM: Artificial Sequence
<220> FEATURE:
<223> OTHER INFORMATION: Synthetic DNA

<400> SEQUENCE: 23
tcgtaagctt agaggcggcg gctgcagacg gagcgcggtg tt                      42

<210> SEQ ID NO 24
<211> LENGTH: 32
<212> TYPE: DNA
<213> ORGANISM: Artificial Sequence
<220> FEATURE:
<223> OTHER INFORMATION: Synthetic DNA

<400> SEQUENCE: 24
acgaagatct cattacccca aatagcatca ca                                 32
```

<210> SEQ ID NO 25
<211> LENGTH: 41
<212> TYPE: DNA
<213> ORGANISM: Artificial Sequence
<220> FEATURE:
<223> OTHER INFORMATION: Synthetic DNA

<400> SEQUENCE: 25
tcgtaagctt agaggcggcg gctgcagacg gagcgcggtg t                 41

<210> SEQ ID NO 26
<211> LENGTH: 33
<212> TYPE: DNA
<213> ORGANISM: Artificial Sequence
<220> FEATURE:
<223> OTHER INFORMATION: Synthetic DNA

<400> SEQUENCE: 26
acgaaccggt cagaagtggt gaagccagcc tgc                          33

<210> SEQ ID NO 27
<211> LENGTH: 36
<212> TYPE: DNA
<213> ORGANISM: Artificial Sequence
<220> FEATURE:
<223> OTHER INFORMATION: Synthetic DNA

<400> SEQUENCE: 27
tcgtaccggt acaggctctg ggaagtagga gaaagt                       36

<210> SEQ ID NO 28
<211> LENGTH: 32
<212> TYPE: DNA
<213> ORGANISM: Artificial Sequence
<220> FEATURE:
<223> OTHER INFORMATION: Synthetic DNA

<400> SEQUENCE: 28
acgaagatct cattacccca aatagcatca ca                           32

<210> SEQ ID NO 29
<211> LENGTH: 6120
<212> TYPE: DNA
<213> ORGANISM: Human

<400> SEQUENCE: 29
cattacccca aatagcatca cattctatct ctggatcacc atttttacac ttatctagaa    60
tttgcccacc tgtagtttcc actcttcggc actaattatt ttgcttaatt gcgtacagaa   120
caaatctacc ccgtccactg tctatgcctt caagtatctg agaacagtaa tgtcctgttc   180
ggtaagtcat tttctccttt tcactctctg gtccttccat ggggcttcaa tccccataca   240
cctctttttt ctaaatttca taggtcagtt ttcctgtctc ttctaccagg ttctactgaa   300
gatgaaaaaa agtgcttttt taaaccaaaa gtattgcaat gtttatttta tctttgtaag   360
ttccttagta atatatacaa atcaagtaaa agatatatgt tgcatgtgat atttttaactt   420 ttgatatgac ttattgaaaa aatatataag gatacatagc cattgtgtgt cttcaaatca   480
taggaaagta tcatgtcgcg aatgtattgg gaaggcagtt ggggtatcac gtagtagttg   540
agagttaggg ggtcaggcag atcctcagtg taccatttac tggttccgtg acctaggaga   600
agttatttaa cttctctgag cctctgagtt tcctcatcag tgaagtggga ataacaataa   660

-continued

```
tatatgcctc caaaggccgc aatgaggact aactgtgtta agttttgtaa aatgcctaaa      720
atattatagt gtctggcact tgttcaatgc tatgtatttg ttaaatacat gacatgaata      780
aatctttcat tgagttatga ggattaggta catcaggtgc ttagcataaa gagtgattta      840
ttaataagaa taggctcatg atgcaggaat attcatcaca tatgtaaata atctgaagct      900
cagagaagtt aagtaatttg gccatgctta cccagtcagt tattatctta gtgagaattt      960
gaacatgggc ctcctggtct cttaatcacc atgctatacc acttatatca gcatagaaat     1020
ggaatatttt ctccttaacg cagagtttga tagtctttgt ctctttgtat tgggctggac     1080
taagaaaacc caatcctgtc ctcttttctac ttttctctg ttcctaagag cactccctt      1140 tctctgttgt atatcagttc ctaatggtag acacttgagc accactattc tgtacagctc     1200
tccgacaatc ccacatctag atgccaagct gaggttggca ttctcactaa tttgctgtta     1260
taaatattaa gctatcataa gcgttagcct acatatgact ctttcatatg ttagttaatt     1320
attttagggt agaaatccaa aagtggagtt accagaagtg gatatagaca ttctggctgg     1380
gtgtgatggt tcatgcctgt aatcccagca ctttgggagg cagaggcagg cggatcactt     1440
gaggccagga gtttgagatc agcctgggcc aacacagcga aaccccatct ctactaaaaa     1500
ttccaaaact agccaggcat agtggcacat gcctgtactc ccagctactt gggaggctaa     1560
gacacaagaa tcgcttgaac ccgggaggga ggtggaggtt gcggtgagct gagattgtgc     1620
caccgtactc cagcctgggt gacacagcta gactctgttc aaaaaaaaaa aagaaaaaga     1680
aaagaaaaaa atagactttc tcttggctca gtgtatactg ccaaattgtt ttccaaaaaa     1740
attgtgtcaa tgtataacac catcactaat atagtattga tattatggtt attacatttt     1800
aaaattcata atttgtaatt ataacattca taatttatta ctatttataa tattaatgta     1860
aatgtatatt atatataaat gttatagtaa ttataacttt ggtagtgaca aagtattaat     1920
ttattaggtg aagtatatgc ttttttatta gtgataataa atatatcctc tctcccatta     1980
taaaagtttg tatttcttct tttagaaatt gattcttctg tcatttgcac atttatctgt     2040
ataattataa cagggtattt cccagtggtg gctaatgaga gaattatggg aaagtataga     2100
acactattca aatgcaaagc actgtatgat ttttatttaa taggaagaca ttttgtgcag     2160
cgatttctga ttgaccacag tttgatcaag tgcatttgtt aatgtgttct acattttcaa     2220
aaaggaaagg agaatttgtt acattcagaa cttgctgcca ctcctttgct acgtcataaa     2280
gggtcagttg cccttgctca tactgaccta ttctttacct ctctgcttct tctttgtgcc     2340
agaagagtag aaatctgacc cttgggggat accaccctct cccctactgc tctctccaac     2400
ctgaggcaaa ctttctccta cttcccagag cctgtcagaa gtggtgaagc cagcctgctc     2460
cttggaatcc agaactactt tcagaatctt gaacttctgt gacctctcag ggtccccttg     2520
tgtgaagttt ttgacgtcag cttctcctgt gacccttaga agtcactctt gtgtctagca     2580
catcccaggt gctcagtcac cattgaacta cagtcatact atctcctggc aaaggctctt     2640
aactgtccat gttagcctga tattaatatc ctggaagctt atactgtcgt tcttccttcc     2700
aggtttaaat aaggcagccc ctttatcctg tcacaggtcc tctctcccta cctatcctta     2760
cctgttttgg ataacaacct ttcttatttc taatagattt atttatttct cacatttcct     2820
tcccttatca tagttttcct ctcactttct cctctagttt gtcatactct ggctttaaaa     2880
catgcaaaca tgtgccttat ggggaaaaaa agacaatttt aatttacctt gcttcttctt     2940
tacaaatgta ttgtggcttc ttcttatagt ccaaatctaa aactctttac ccacccactg     3000
ccttgaactc cttcctcgtt gtgaaagtag gatggggcaa agagagaatg catgcccctc     3060
```

```
ccaactgctc aaacaagtaa aggtgctgtt acagttatct tttgctacct taatacaata    3120
attattttat tatatctcac aatttatgg atcaggaatt tagactgggc tcagctaggc     3180
gattcttctg ctttactgac atcataggag atcacttggt ggtattcaac tgtcaggtag    3240
gcttatctgg agggtccaag atagctgtac tctggtgcct ggtgccttgg taaagaggga    3300
tgatgatgtg gggcctctcc agcatgaaca gcctcagaga agtttgcttt cttacatgct    3360
ggcccagggc tccaagagca aatgttgcag tgagtaaagc agaagataca aggacttta     3420 taatctggtc tcagaagcca catggcatca gttctgtatt attctattgg tcaaaacatt    3480
cataagcctg ccagatgcaa ggggaaggca tatgtaccct catcttttga tgggaggaat    3540
gtgatggatt tgcaattatg ttttaaaact actacagaca gaaccactga gaaagattca    3600
tgggtagctt tggggtgagg actgggaatt aacctgttga tagcagaggt tcactagagt    3660
caacaaggaa taaggtctcc tcttgtacac tttagtcata ctataccaac attcttaacc    3720
actgcttagc catcagcctc acaacataac aactccatca tagttgtact ccctaagatc    3780
accaacaatg ttagagtcaa atccggtagg tttttctttg tttttgtcct cctgacattt    3840
tttctaaact tgacactggt cagacccaat cttctttaa tcatattctt aaataccagt     3900
tctatcactg gatatgttac tgtttcttgt tctcactcta cctttgacaa agccattctt    3960
tccagactat aactctgggt ctgggtcccc ctatggtttg gcccttgaat tcttttccta    4020
gtcctatttg actagcccca ttttcccgtg aaaagcatgc cccttcatt gcatccatat     4080 catgactacc aaatacctcc tctatttctt cctcttttag catgttaaat gcagcttcct    4140
aagctctcta tctggatatc aacagtattc tctccaaata attctaagac tttaaaaatt    4200
ggtttaatct tcttaccct aaaatcaccc cccttaccaa ctgcctcatg acaatcattg      4260
gtactgtcac tgagcttgca acccatgttc ttaaacatag agtaatcttt gactccacat    4320
ctaatcattc ataaagctgt attgtctatc aaattaaatc tgacatttat gtgagagcac    4380
ttcatagtct gtaaagcact acacaggtga taacatgaag ctacactcat aatggatttg    4440
caggctctgc ttctcatttg gcttctacag cctcatccct caccaacttc ttgccctacc    4500
tctctctttc ttccccatca cccaatttcc cagtcagtca ggccaacaga atgcattcta    4560
tatacgcgac ttgctttccc caacatcttt gcctgtatgc atgccactta tttgcctcag    4620
ttgatcttta tttcaacaag tgtttgcaga ggagaaacct cgctggctcc ttctcctttc    4680
tatttttttt cagaggctac ccgtcaggtc aacattgcct ttttcaggga agctctgcaa    4740
gcctgacctc ccttggaagt gccttaggac tggcttcttg cacagtacac aacctttact    4800
tatagagggt ttggagatta ttctttattc atgtcttatt tctcctgctc ctggaggaga    4860
tgactctgac ttccactgac tcttttgggg ggcttaagtc agggttgagt accagaggcc    4920
ctaaatagct ggacgtggat tctggtaata tcaaatccat cttttggctta actgagaggt    4980 tctgaaagct gggacctgac cttgtccatt tccctctttc tccagtttcc tattatttcc    5040
cactgttttt tttaaaagtt ttttgttttc ttaagttttc acaagaataa acattgaaaa    5100
taaaatttgc acaaagatcg aactaggaaa ggccacacaa ccaacacata ttacatcatt    5160
ataggtaagt tagcagggag atttcagacc tgggctagct ctggaaccac attttacact    5220
gttgaaaata aaagctggag tacagatgac tttcccaggt tcacagagtt ggtaagctgg    5280
agagctgcac ctggagccaa gcaacctgcc ctgtcctttc cactgcaccc tctaagaaat    5340
ctaattagaa ggaacaggtg gtatctcatt ttgtacggtg ctttagcaat gtactatttg    5400
```

-continued

```
ctttctagtg tgtctattgt ctcgtttgac atcttctctc aaaaagtgat gaaacgaaac    5460 gctcttttg  acaagttcag agtgctcttg gttcctgtgt gggattcttc caagtctgaa    5520
tttggtagtg ggaagagaag gaatccggag gaaggaggat gagaagttta aaggagagga    5580
aagggaagca gagaaggccg caaggtgcct gcaagatgtc tggggagttg gaggaatgga    5640
agagtgcccc gctcttcctt ctgggagagc tccagctagg cagaaccttt caccaaggct    5700
ctgatatcgt gctggtttcc gaaagcccca gccgaaggtg tgcagccaaa gggtgacaga    5760
aggtgaggca cgtgcggggg cgcgggtgct gaccgccgcg gtgcgccctc cctccgacgt    5820
gcggtgtgcg gggcgcagac aaccagcggc cggcccaggg ctttcgggga gcgaagcagg    5880
gctcccgagg caccgagcga gaatgggaat gggagggacc cggtgctccc ggacacgccc    5940
ccggcaggtc ccacgcccgg gtcttctgag acctcgcgcg gcccagcccg ggagcggccc    6000
agctatataa gtcccagcgg aagaccggaa cgcagagggt cctgctggcg cgagggtggg    6060
taggagggga cgcggggact cggcccccaa caccgcgctc cgtctgcagc cgccgcctct    6120

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30
caggaaagtc aagagcacca                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA

<400> SEQUENCE: 31
tcatactggg ccaggaattt                                                  20

<210> SEQ ID NO 32
<211> LENGTH: 20
<212> TYPE: DNA
<213> ORGANISM: Artificial Sequence
<220> FEATURE:
<223> OTHER INFORMATION: Synthetic DNA

<400> SEQUENCE: 32
tgcacatgta ccaggacacc                                                  20
```